US005830699A

United States Patent [19]
Force et al.

[11] Patent Number: 5,830,699
[45] Date of Patent: Nov. 3, 1998

[54] SOK-1 AND METHODS OF USE

[75] Inventors: Thomas Force, Natick; John M. Kyriakis, Dedham, both of Mass.; Celia M. Pombo, Santa Cruz, Spain; Joseph Bonventre, Wayland, Mass.

[73] Assignee: The General Hospital Corporation, Boston, Mass.

[21] Appl. No.: 852,743

[22] Filed: May 7, 1997

Related U.S. Application Data

[60] Provisional application No. 60/016,774, May 7, 1996.
[51] Int. Cl.[6] ............................. C12P 21/06; C12N 9/00; C07K 14/00
[52] U.S. Cl. ...................... 435/69.1; 435/183; 530/350; 530/300
[58] Field of Search .................................. 435/69.1, 183; 530/350, 300

[56] References Cited

PUBLICATIONS

Hanks et al., Protein Kinase Catalytic Domain Sequence Database: Identification of Conserved Features of Primary Structure and Classification of Family Members, Methods In Enzymology, vol. 200, 38–62, 1991.
Wu et al., Molecular Characterization of Ste20p, a Potential Mitogen–activated Protein or Extracellular Signal–regulated Kinase Kinase (MEK) Kinase Kinase from *Saccharomyces cerevisiae*, The Journal of Biological Biological Chemistry, vol. 270, No. 27, 15984–15993, 1995.
Ansorge, W. et al., "Performance of an automated system for capillary microinjection into living cells," Journal of Biochemical and Biophysical Methods, 16:283–292 (1988).
Brown, D. et al., "Antigen retrieval in cryostat tissue sections and cultured cells by treatment with sodium dodecyl sulfate (SDS)," Histochem. Cell Biol. 105:261–267 (1996).
Bruder, J.T. et al., "Serum–, TPA–, and Ras–induced expression from Ap–1/Ets–driven promoters requires Raf–1 kinase," Genes & Development 6:545–556 (1992).
Chen J., et al., "Regulation of Protein Serine–Threonine Phosphatase Type–2A by Tyrosine Phosphorylation," Science 257:1261–1264 (1992).
Creasy, C.L. et al., "Cloning and Characterization of a Human Protein Kinase with Homology to Ste20," J. Biol. Chem. 270:21695–21700 (1995).
van Dam, H. et al., "ATF–2 is preferentially activated by stress–activated protein kinases to mediate c–jun induction in response to genotoxic agents," EMBO J. 14:1798–1811 (1995).
Friesen, H. et al., "Mutation of the SPS1–encoded protein kinase of *Saccharomyces cerevisiae* leads to defects in transcription and morphology during spore formation," Genes & Development 8:2162–2175 (1994).
Galcheva–Gargova, Z. et al., "An Osmosensing Signal Transduction Pathway in Mammalian Cells," Science 265:806–808 (1994).

Guan, K. et al., "Eukaryotic Proteins Expressed in *Escherichia coli*: An Improved Thrombin Cleavage and Purification Procedure of Fusion Proteins with Glutathione S–Transferase", Anal. Biochem. 192:262–267 (1991).
Han, J. et al., "A MAP Kinase Targeted by Endotoxin and Hyperosmolarity in Mammalian Cells," Science 265:808–811 (1994).
Hanks S.K. et al., "Protein Kinase Catalytic Domain Sequence Database: Identification of Conserved Features of Primary Structure and Classifications of Family Members," Methods Enzym. 200:38–81 (1991).
Herskowitz, I., "MAP Kinase Pathways in Yeast: For Mating and More," Cell 80:187–197 (1995).
Hibi, M. et al., "Identification of an oncoprotein–and UV–responseive protein kinase that binds and potentiates the c–Jun activation domain," Genes & Development 7:2135–2148 (1993).
Katz, P. et al., "Differential Expression of a Novel Protein Kinase in Human B Lymphocytes," J. Biol. chem. 269:16802–16809 (1994).
Kharbanda, S. et al., "Activation of the c–Abl tyrosine kinase in the stress resonse to DNA–damaging agents," Nature 376:785–788 (1995).
Kharbanda, S. et al., "Ionizing Radiation Stimulates a Grb2–mediated Association of the Stress–activated Protein Kinase with Phosphatidylinositol 3–Kinase," J. Biol. chem. 270:18871–18874 (1995).
Krisak, L. et al., "SMK1, a developmentally regulated MAP kinase, is required for spore wall assembly in *Saccharomyces cerevisiae*," Genes & Development 8:2151–2161 (1994).
Kyriakis, J. M. et al., "The stress–activated protein kinase subfamily of c–Jun kinases," Nature 369:156–160 (1994).
Leberer, E. et al., "The protein kinase homologue Ste20p is required to link the yeast pheromone response G–protein βγ subunits to downstream signalling components," EBMO J. 11:4815–4824 (1992).
Livingstone, C. et al., "ATF–2 contains a phosphorylation–dependant transcriptional activation domain," EMBO J. 14:1785–1797 (1995).
Manser, E. et al., "A brain serine/threonine protein kinase activated by Cdc42 and Rac1," Nature 367:40–45 (1994).

(List continued on next page.)

*Primary Examiner*—Karen Cochrane Carlson
*Attorney, Agent, or Firm*—Fish & Richardson P.C.

[57] ABSTRACT

A SOK polypeptide, an isolated DNA having a nucleotide sequence encoding a SOK polypeptide, and a method of determining whether a candidate compound modulates SOK-1 activity or expression, comprising the steps of providing a first and a second recombinant cell expressing a SOK gene; introducing a candidate compound into the first cell, but not into the second cell; measuring a SOK function in the first and second cells; and comparing the results obtained with the first and second SOK transformed cells, wherein an increase or decrease in the SOK function in the first cell compared to the second cell is an indication that the candidate compound modulates SOK expression or activity.

16 Claims, 6 Drawing Sheets

OTHER PUBLICATIONS

Martin, G. A., "A novel serine kinase activated by rac1/CDC42Hs–dependent autophosphorylation is related to PAK65 adn STE20," EMBO J. 14:1970–1978 (1995).

Morooka, H. et al., "Ischemia and Reperfusion Enhance ATF–2 and c–jun Binding to cAMP Response Elements and to an AP–1 Binding Site from the c–jun Promoter," J. Biol. Chem. 270:30084–30092 (1995).

Osada, S. et al., "YSK1, a novel mammalian protein kinase structurally related to Ste20 and SPS1, but is not involved in the known MAPK pathways," Oncogene 14:2047–2057 (1997).

Pagano, M. et al., "Cyclin D1–mediated inhibition of repair and replicative DNA synthesis in human fibroblasts," Genes & Development 8:1627–1639 (1994).

Polverino, A. et al., "Activation of Mitogen–activated Protein Kinase Cascades by p21–activated Protein Kinases in Cell–free Extracts of Xenopus Oocytes," J. Biol. Chem. 270:26067–26070 (1995).

Pombo, C. M. et al., "The Stress–activated Protein Kinases Are Major c–Jun Amino–terminal Kinases Activated by Ischemia and Reperfusion," J. Biol. Chem. 269:26546–26551 (1994).

Pombo, C. M. et al., "Activation of the SAK pathway by the human STE20 homologue germinal centre kinase," Nature 377:750–754 (1995).

Pombo, C. M. et al., "Activation of a human Ste20–like kinase by oxidant stress defines a novel stress response pathway," EMBO J. 15:4537–4546 (1996).

Radler–Pohl, A. et al., "UV–induced activation of AP–1 involves obligatory extranuclear steps including Raf–1 kinase," EMBO J. 12:1005–1012 (1993).

Rouse, J. et al., "A Novel Kinase Cascade Triggered by Stress and Heat Shock That Stimulates MAPKAP Kinase–2 and Phosphorylation of the Small Heat Shock Proteins," Cell 78:1027–1037 (1994).

Russo, T. et al., "A p53–independent Pathway for Activation of WAF1/CIP1 Expression Following Oxidative Stress," J. Biol. Chem. 270:29386–29391 (1995).

Sanchez, I. et al., "Role of SAPK/ERK kinase–1 in the stress–activated pathway regulating transcription factor c–Jun," Nature 372:794–798 (1994).

Verma, I. M. et al., "Rel/Nf–kB/IkB family: intimate tales of association and dissociation," Genes & Development 9:2723–2735 (1995).

Witzgall, R. et al., "Kid–1, a Putative Renal Transcription Factor: Regulation during Ontogeny and in Response to Ischemia and Toxic Injury," Mol. Cell. Biol. 13:1933–1942 (1993).

Zhou, G. et al., "Components of a New Human Protein Kinase Signal Transduction Pathway," J. Biol. Chem. 270:12665–12669 (1995).

```
                                                                caccga
gcgcccctggtgtccctcgtagtggactgacgccgcagggcgagctagccggctccgcgc
ctctccgcggatccagacgcctcctggggctgctggcggagggtctgaggcggcgcggcc
atggctcacctccggggatttgcaaaccagcactctcgsgtggaccctgaggagctcttc  60
 M  A  H  L  R  G  F  A  N  Q  H  S  R  V  D  P  E  E  L  F   20
accaagctcgaccgcattggcaagggctcgtttggggaggtctacaagggcatcgataac 120
 T  K  L  D  R  I  G  K  G  S  F  G  E  V  Y  K  G  I  D  N   40
cacacaaaggaggtggtggccatcaagatcatcgacctggaggaggccgaggatgagatc 180
 H  T  K  E  V  V  A  I  K  I  I  D  L  E  E  A  E  D  E  I   60
gaggacatccagcaggagatcactgtcctcagtcagtgcgacagcccctacatcacccgc 240
 E  D  I  Q  Q  E  I  T  V  L  S  Q  C  D  S  P  Y  I  T  R   80
tactttggctcctacctaaagagcaccaagctatggatcatcatggagtacctgggcggc 300
 Y  F  G  S  Y  L  K  S  T  K  L  W  I  I  M  E  Y  L  G  G  100
ggctcagcactggacttgcttaaaccaggtcccctggaggagacatacattgccacgatc 360
 G  S  A  L  D  L  L  K  P  G  P  L  E  E  T  Y  I  A  T  I  120
ctgcgggagattctgaagggcctggattatctgcactccgaacgcaagatccaccgagac 420
 L  R  E  I  L  K  G  L  D  Y  L  H  S  E  R  K  I  H  R  D  140
atcaaagctgccaacgtgctactctcggagcagggtgacgtgaagctggcggactttggg 480
 I  K  A  A  N  V  L  L  S  E  Q  G  D  V  K  L  A  D  F  G  160
gtagcagggcagctcacagacacgcagattaagaggaacacattcgtgggcacccccttc 540
 V  A  G  Q  L  T  D  T  Q  I  K  R  N  T  F  V  G  T  P  F  180
tggatggcacctgaggtcatcaagcagtcggcctacgacttcaaggctgacatctggtcc 600
 W  M  A  P  E  V  I  K  Q  S  A  Y  D  F  K  A  D  I  W  S  200
ctgggcatcacagccatcgagctggccaaggggagcctccaaactctgacctccacccc 660
 L  G  I  T  A  I  E  L  A  K  G  E  P  P  N  S  D  L  H  P  220
atgcgcgtcctgttcctgattcccaagaacagcccacccacactggagggccagcacagc 720
 M  R  V  L  F  L  I  P  K  N  S  P  P  T  L  E  G  Q  H  S  240
aagcccttcaaggagttcgtggaggcctgcctcaacaaagacccccgattccggcccacg 780
 K  P  F  K  E  F  V  E  A  C  L  N  K  D  P  R  F  R  P  T  260
gccaaggagctcctgaagcacaagttcatcacacgctacaccaagaagacctccttcctc 840
 A  K  E  L  L  K  H  K  F  I  T  R  Y  T  K  K  T  S  F  L  280
acggagctcatcgaccgctataagcgctggaagtcagaggggcatggcgaggagtccagc 900
 T  E  L  I  D  R  Y  K  R  W  K  S  E  G  H  G  E  E  S  S  300
tctgaggactctgacattgatggcgaggcggaggacggggagcagggccccatctggacg 960
 S  E  D  S  D  I  D  G  E  A  E  D  G  E  Q  G  P  I  W  T  320
ttccccccctaccatccggccgagtccacacagcaagcttcacaaggggacggccctgcac 1020
 F  P  P  T  I  R  P  S  P  H  S  K  L  H  K  G  T  A  L  H  340
agttcacagaagcctgcggacgccgtcaagaggcagccgaggtcccagtgcctgtccacg 1080
 S  S  Q  K  P  A  D  A  V  K  R  Q  P  R  S  Q  C  L  S  T  360
ctggtccggcccgtcttcggagagctcaaagagaagcacaagcagagcggcgggagcgtg 1140
 L  V  R  P  V  F  G  E  L  K  E  K  H  K  Q  S  G  G  S  V  380
ggtgcgctggaggagctggagaacgccttcagcctggccgaggagtcctgccccggcatc 1200
 G  A  L  E  E  L  E  N  A  F  S  L  A  E  E  S  C  P  G  I  400
tcagacaagctgatggtgcacctggtggagcgagtgcagaggttttcacacaacagaaac 1260
 S  D  K  L  M  V  H  L  V  E  R  V  Q  R  F  S  H  N  R  N  420
cacctgacatccacccgctgaagcgcactgctgttcagataggggacggaaggtcgtttg 1320
 H  L  T  S  T  R  *                                          426
tttttgttctgagctccataagaactgtgctgacttggaaggtgccctgtgctatgtcgt 1380
gcctgcagggacacgtcggatcccgtgggcctcacatgccaggtcaccaggtcaccgtct 1440
ccttccacccctgcagtgtgctgttgtgcacgtcaggacgctgttctctatgccactgcc 1500
tcctccctctcctggcccagcagtattgctcacggggctccagccgccggcgtggccct 1560
catgagctacgcctgggtcttctgcagactcatgcagccctatggccgctcagaccaagg 1620
cgcagagcaactatcagggcatgctctgcctcctcctcccattgaggtggggagaggcaa 1680
cagggcagccccagaggagtgtcctggccgctgtctcccgggcccatgatggccataga 1740
tttgccttgtggtgttccatcaggtactgtgtctgctcataagtacttgtgtcatccaga 1800
atgttttgttttttaagaaaattgaattacttgtttcctgaaaaaaaa            1849
```

FIG. 1

```
                              I                   II
      PAK1   PKKKYTRFEK   IGQGASGTVY   TAMDVATGQE   VAIKQMNLQQ   .QPKKELIIN
      Ste20  PSTKYANLVK   IGQGASGGVY   TAYEIGTNVS   VAIKQMNLEK   .QPKKELIIN
      MST1   PEEVFDVLEK   LGEGSYGSVY   KAIHKETGQI   VAIKQVPV..   .ESDLQEIIK       65
      SOK-1  PEELFTKLDR   IGKGSFGEVY   KGIDNHTKEV   VAIKIIDLEE   AEDEIEDIQQ
      Sps1   PSKLYSIQSC   IGRGNFGDVY   KAVDRVTQEI   VAIKVVNLEH   SDEDIELLAQ
      GCK    PRDRFELLQR   VGAGTYGDVY   KARDTVTSEL   AAVKIVKLD.   PGDDISSLQQ

III           IV            V
      PAK1   EILVMRENKN   PNIVNYLDSY   LVGDELWVVM   EYLAGGSLTD   VV...TETCM
      Ste20  EILVMKGSKH   PNIVNFIDSY   VLKGDLWVIM   EYMEGGSLTD   VV...THCIL
      MST1   EISIMQQCDS   PHVVKYYGSY   FKNTDLWIVM   EYCGAGSVSD   IIRLR.NKTL      112
      SOK-1  EITVLSQCDS   PYITRYFGSY   LKSTKLWIIM   EYLGGGSALD   L..LK.PGPL
      Sps1   EIFFLAELKS   PLITNYIATM   LEDVSMWIVM   EYCGGGSCSD   LLKRSYVNGL
      GCK    EITILRECRH   PNVVAYIGSY   LRNDRIWICM   EFCGGGSLQE   IYH..ATGPL

VI                  VII
      PAK1   DEGQIAAVCR   ECLQALEFLH   SNQVIHRDIK   SDNILLGMDG   SVKITDFGFC
      Ste20  TEGQIGAVCR   ETLSGLEFLH   SKGVLHRDIK   SDNILLSMEG   DIKITDFGFC
      MST1   TEDEIATILQ   STLKGLEYLH   FMRKIHRDIK   AGNILLINTEG  HAKIADFGVA      162
      SOK-1  EETYIATILR   EILKGIDYLH   SERKIHRDIK   AANVLLSEQG   DVKIADFGVA
      Sps1   PEEKVSFIIH   EVTLGLKYLH   EQRKIHRDIK   AANILLINEEG  MVKIGDFGVS
      GCK    ERQIAYVCR    ERLKGLHHLH   SQGKIHRDIK   GANILLITLQG  DVKIADFGVS

VIII                      IX
      PAK1   AQITPEQSKR   STMVGTPYWM   APEVVTRK..   .AYGPKVDIW   SLGIMAIEMI
      Ste20  AQINELNIKR   TTMVGTPYWM   APEVVSRK..   .EYGPKVDIW   SLGIMIIEMI
      MST1   GQLTDTMAKR   NTVIGTPFWM   APEVI..Q.E   IGYNCVADIW   SLGITAIEMA      209
      SOK-1  GQLTDTQIKR   NTFVGTPFWM   APEVI..K.Q   SAYDFKADIW   SLGITAIELA
      Sps1   GHIRSTL.KR   DTFVGTPYWM   APEVVCCE.V   DGYNEKADIW   SLGITTYELL
      GCK    GELTASVAKR   RSFIGTPYWM   APEVAAVERK   GGYNELCDVW   ALGITAIELG

X                       XI
      PAK1   EGEPPYLNEN   FLRALYLIAT   NG..TPELQN   PEKLSAIFRD   FLNRCIEMDV
      Ste20  EGEPPYLNET   PLRALYLIAT   NG..TPKLKE   PENLSSSLKK   FLDWCICVEP
      MST1   EGKRPYADIH   PMRAIFMIPT   NP..PPTFRK   PELWSDNFTD   FVKQCIVKSP      255
      SOK-1  KGEPPNSDLH   PMRVLFLIPK   NS..PPTLEG   QH..SKPFKE   FVEACINKDP
      Sps1   KGLPPLSKYD   PMKVMTNLPK   RK..PPKLQG   P..FSDAAKD   FVAGCLVKTP
      GCK    ELQPPLFHLH   PMRALMLMSK   SSFQPPEKLRD  KTRWTQNFHH   ELKLAITKNP

PAK1   EKRGSAKELI   QHQFL.KIAK   PLSSITPL..
      Ste20  EDRASATELI   HDEYITEIAE   ANSSLAPLVK
      MST1   EQRATATQLI   QHPFV.RSAK   GVSILRDLIN
      SOK-1  RFRPTAKELI   KHKFITRYTK   KTSFLTELID     285
      Sps1   ADRPSAYNLI   SFEFVKNIT.   .ITNLKSDVD
      GCK    KKRPTAEKLI   QHPFTTQQLP   R.AILTQLLD
```

FIG. 2

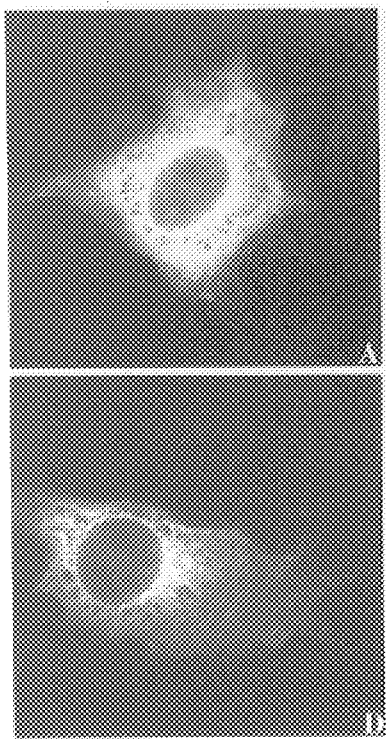
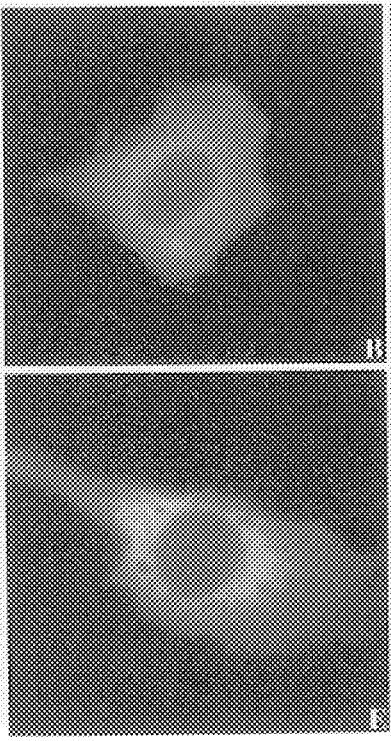
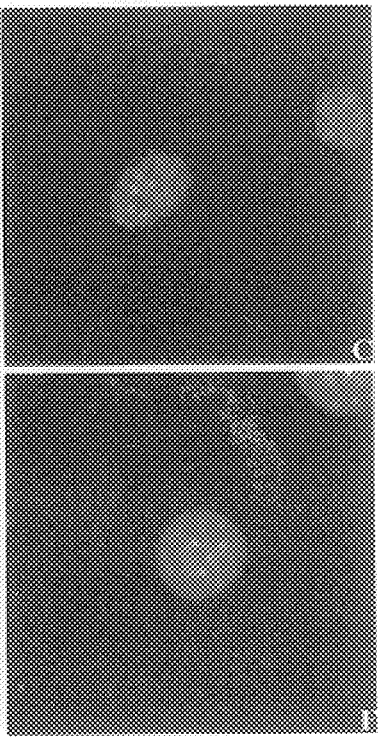
FIG. 5A  FIG. 5B  FIG. 5C
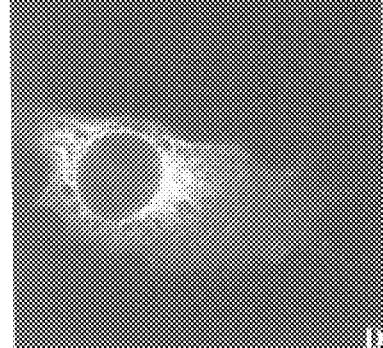
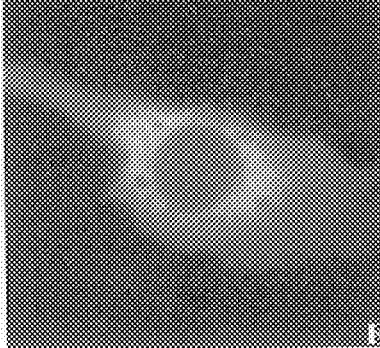
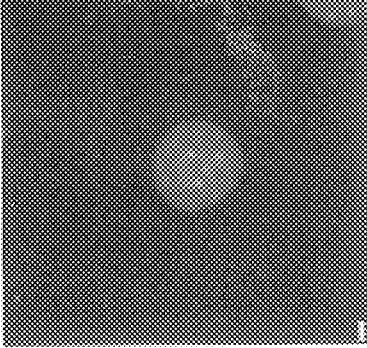
FIG. 5D  FIG. 5E  FIG. 5F
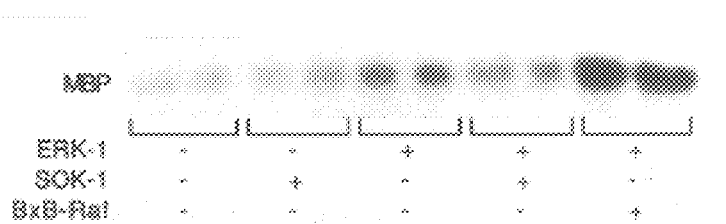
FIG. 9B 5,830,699

1

SOK-1 AND METHODS OF USE

STATEMENT AS TO FEDERALLY SPONSORED RESEARCH

This invention was supported in part by U.S. Public Health Service Grants DK41513, GM46577, DK39773, DK38452 and NS10828, and an award from the NIDDK. The government may have certain rights in the invention.

This application is a continuation in part of provisional application U.S. Ser. No. 60/016,774, filed May 7, 1996.

BACKGROUND OF THE INVENTION

The invention relates to protein kinases and methods of activating or inhibiting the expression of protein kinases.

Mitogen-activated protein kinase (MAPK) cascades have been remarkably conserved in evolution. The core of these cascades is a three-tiered module of serine/threonine kinases that consists of a MAPK-extracellular signal regulated kinase kinase (a MEKK), a MEK, and a MAPK or extracellular signal regulated kinase (ERK). In simple eukaryotes, such as the budding yeast *Saccharomyces cerevisiae* (*S. cerevisiae*), and the fission yeast, *Saccharomyces pombe* (*S. pombe*), these cascades are activated predominantly by cellular stresses such as nutritional starvation and osmolar stress (reviewed in Elion, *TIBS* 5:322 (1995); Herskowitz, *Cell* 80:187 (1995); and Levin et al., *Cell Biol.* 7:197 (1995)). In mammals, these cascades have evolved to allow responses to complex stimuli (e.g., growth factors and inflammatory cytokines), but in many cases, such as the response to osmolar challenge (Galcheva-Gargova et al., *Science* 265:806 (1994); Han et al., *Science* 265:808 (1994)), the primitive stress responses remain intact.

Epistasis analyses in yeast suggest that the Sterile 20 (Ste20) protein serine/threonine kinases and related protein kinases act upstream of the three tiered module. Three mammalian homologs of Ste20 have been reported to date: p21-activated protein kinase (PAK1) and related PAKs (Manser et al., *Nature* 367:40 (1994); Martin et al., *EMBO J.* 14:1970 (1995)); germinal center (GC) kinase (Katz et al., *J. Biol. Chem.* 269:16802 (1994)); and mammalian Ste20-like kinase 1 (MST1) (Creasy et al., *J. Biol. Chem.* 270:21695 (1995)). Mammalian Ste20s may function upstream of MEKK/MEK/MAP kinase pathways. PAK1 (Manser et al., *Nature* 367:40 (1994)) and GC kinase (Katz et al., *J. Biol. Chem.* 269:16802 (1994)) have been shown to be capable of activating mammalian MAPK kinases (Polverino et al., *J. Biol. Chem.* 270:26067 (1995); Pombo et al., *Nature* 377:750 (1995); Zhang et al., *J. Biol. Chem.* 270:12665 (1995)), further illustrating remarkable evolutionary conservation of the MAPK kinases. When co-transfected with MAP kinase, both PAK1 and GC kinase activate the stress-activated protein kinase (SAPK)/c-Jun amino terminal kinase (JNK) cascade. PAK1 also activates the stress activated MAPK, p38, as well.

Ste20 protein kinases can be divided into two families based on their structure and regulation. The first family is the Ste20 family, which includes Ste20, PAK1 and related PAKs. These proteins contain a carboxy terminal catalytic domain and an amino terminal regulatory domain which has a $p21^{cdc42/rac1}$ binding region (Manser et al., *Nature* 367:40 (1994); Martin et al., *EMBO J.* 14:1970 (1995)). PAK1 appears to be activated by binding to cdc42Hs or Rac1. Following binding to the small GTP-binding proteins, the kinase undergoes autophosphorylation and is activated. Physiologic activators of PAK1 have been identified, and include the chemoattractant peptide fMetLeuPhe, and Interleukin 1 (IL-1) (Zhang et al., *J. Biol. Chem.* 270:12665 (1995)).

2

The second family of Ste20s is the Sps1 family. Members of this group include Sps1, which is encoded by the *S. cerevisiae* Sporulation specific 1 gene, which is necessary for spore formation in response to nutritional starvation; and the mammalian genes MST1 and GC kinase. The catalytic domain is amino terminal in these proteins, and the function of their carboxy terminal regions has not previously been known. These kinases do not contain an identifiable Rac/cdc42Hs binding domain in their non-catalytic regions. The regulation of this family of Ste20s is not well characterized. MST1 appears to be activated by dephosphorylation. Sps1 and its MAPK, Smk1 (Krisak et al., *Genes & Development* 8:2151 (1994)), are transcriptionally regulated, being expressed only at certain stages of the sporulation process, but it is not known if there are other modes of regulation of Sps1. Physiological activators of the Sps1 family of Ste20s have not been previously identified.

SUMMARY OF THE INVENTION

The invention is based on the discovery of a novel mammalian protein kinase, SOK-1, that belongs to the Sps1 family of Ste20 homologs. SOK-1 (Ste20 oxidant stress response kinase 1) is a protein kinase which is activated by oxidant stress (e.g., 0.5 mM $H_2O_2$).

Accordingly, the invention features an isolated nucleic acid encoding a SOK polypeptide, particularly SOK-1. The naturally occurring SOK polypeptide can be from a mammal, such as a human, non human primate, e.g., baboons, monkeys and chimpanzees, goats, pigs, micropigs, guinea pigs, rabbits, rats and mice. This nucleic acid encodes an amino acid sequence with at least 50% (preferably at least 60%, more preferably at least 70%, more preferably at least 85%) identity to the amino acid sequence set forth in FIG. 1 (SEQ ID NO:2). The invention also features a substantially pure preparation of a SOK polypeptide. The SOK polypeptide preferably has an amino acid sequence with at least 50% sequence identity to the sequence set forth as SEQ ID NO:2. Preferably, the sequence has at least 60%, 70% or 85% sequence identity to the sequence set forth as SEQ ID NO:2. By "SOK polypeptide" is meant all or part of a novel protein kinase, expression of which is activated by oxidant stress.

By "isolated" is meant that the DNA is free of the coding sequences of those genes that, in the naturally-occurring genome of the organism (if any) from which the DNA of the invention is derived, immediately flank the gene encoding the DNA of the invention. The isolated DNA may be single-stranded or double-stranded, and may be genomic DNA, cDNA, recombinant hybrid DNA, or synthetic DNA. It may be identical to a naturally-occurring DNA sequence, or may differ from such sequence by the deletion, addition, or substitution of one or more nucleotides. The DNAs of the invention therefore include, e.g., a recombinant nucleic acid incorporated into a vector, such as an autonomously replicating plasmid or virus; a cDNA or genomic DNA fragment produced by polymerase chain reaction (PCR) or restriction endonuclease treatment; and recombinant DNA which is part of a hybrid gene encoding additional polypeptide sequences.

Also included in the isolated DNAs of the invention are single-stranded DNAs which are generally at least 10 nucleotides long, preferably at least 18 nucleotides long, more preferably at least 30 nucleotides long, and ranging up to full length of the DNAs encoding a SOK polypeptide.

The single stranded DNAs can also be complementary to a SOK coding strand, so that they can be labelled and used as hybridization probes. Preferably the isolated DNA or its complement hybridizes under stringent conditions to all or part of the nucleotide sequence shown in FIG. 1 (SEQ ID NO:2). "Stringent conditions" include, for example, hybridization at 68° C. in 5×SSC/5×Denhardt's solution/1.0% SDS, or in 0.5M NaHPO4 (pH 7.2)/1 mM EDTA/7% SDS, or in 50% formamide/0.25M NaHPO4 (pH 7.2)/0.25M NaCl/1 mM EDTA/7% SDS; and washing in 0.2×SSC/0.1% SDS at room temperature or at 42° C., or in 0.1×SSC/0.1% SDS at 68° C., or in 40 mM NaHPO4 (pH 7.2)/1 mM EDTA/5% SDS at 50° C., or in 40 mM NaHPO4 (pH 7.2) 1 mM EDTA/1% SDS at 50° C. Moderately stringent conditions including washing in 3×SSC at 42° C. The parameters of salt concentration and temperature can be varied to achieve the desired level of identity between the probe and the target DNA. For guidance regarding such conditions see, e.g., Sambrook et al., *Molecular Cloning, A Laboratory Manual*, Cold Spring Harbor Press, Cold Spring Harbor, N.Y.; and Ausubel et al., *Current Protocols in Molecular Biology*, John Wiley & Sons, 1995.

DNAs of the invention can be incorporated into a vector, which may be provided as a purified preparation. DNA, either by itself, or incorporated into a vector, can be incorporated into a cell, and the cell can be propagated to form an essentially homogenous population of cells (e.g., prokaryotic cells, or eukaryotic cells such as mammalian cells) containing SOK, by methods that are well known to those skilled in the art. An "essentially homogenous" population of cells is one in which at least 99% of the cells contain the vector or the isolated DNA of the invention.

A further aspect of the invention is a method of determining whether a candidate compound modulates the expression or activity of SOK. The method includes the steps of:

a) providing a first and a second recombinant cell expressing a SOK gene;

b) introducing a candidate compound into the first recombinant cell, but not into the second cell;

c) measuring a SOK function in the first and second cells;

d) comparing the results obtained with the first and second SOK-transformed cells, wherein an increase or decrease in the SOK function in the first cell compared to the second cell is an indication that the candidate compound modulates SOK expression or activity.

In one embodiment of this method, the SOK function to be measured is activation of the gene encoding the transcription factor NFκB. In another embodiment, the function to be measured is protein kinase activity. In other embodiments, the function is arrest of the cell cycle or activation of SOK by $H_2O_2$.

The invention also features a therapeutic composition that includes a SOK polypeptide or DNA as an active ingredient. Such therapeutic compositions can be formulated with a pharmaceutically acceptable carrier. In another aspect, the invention is a method of administering a therapeutically effective amount of a composition of a SOK polypeptide or DNA, or a fragment thereof, to a mammal, to treat a condition characterized by a proliferative response, e.g., to treat a vessel that has sustained balloon angioplasty-induced injury. A "therapeutically effective" amount is an amount that produces a medically desirable result in a patient.

A method of producing a SOK polypeptide is also included in the invention. In this method, cells containing an isolated DNA encoding a SOK polypeptide are cultured under conditions permitting the expression of the SOK polypeptide, and the SOK polypeptide is isolated. Also included in the invention are therapeutic compositions that include DNAs encoding a SOK polypeptide.

In another aspect, the invention is a substantially pure antibody which specifically binds SOK. An antibody that "specifically binds" to SOK binds to SOK and does not substantially recognize and bind to other antigenically-unrelated molecules. Antibodies according to the invention can be prepared by a variety of methods. For example, a SOK protein or antigenic fragment thereof can be administered to an animal in order to induce the production of polyclonal antibodies. Alternatively, the antibodies can be monoclonal antibodies. Such monoclonal antibodies can be prepared using hybridoma technology (see, e.g., Kohler et al., *Nature* 256:495 (1975); Kohler et al., *Eur. J. Immunol.* 6:292 (1976); Kohler et al., *Eur. J. Immunol.* 6:511 (1976); Hammerling et al., *In Monoclonal Antibodies and T Cell Hybridomas*, Elsevier, N.Y., 1981).

As used herein, "substantially pure" describes a molecule, e.g., a protein, that is substantially free from the components that naturally accompany it. Typically, a compound is substantially pure when at least 60%, more preferably at least 75%, more preferably at least 90%, and most preferably at least 99%, of the total material in a sample is the molecule of interest.

Individuals skilled in the art will recognize that the compositions of the invention can be assembled in. a kit for the detection of SOK polypeptides or RNA. Typically, such kits include reagents containing the DNAs or antibodies of the invention with instructions and suitable packaging for their use as part of an assay for SOK. For example, a kit can contain an anti-SOK antibody that is capable of specifically forming an immunocomplex with SOK in a sample, a solid support to which the antibody is bound, and means to detect the immunocomplex.

In another aspect, the invention features a kinase inactive mutant of a SOK polypeptide, or a DNA encoding such a mutant. By "kinase inactive mutant" is meant a SOK polypeptide which has been altered so that the kinase domain is less active than in the wild-type SOK. Such mutants preferably show 50% or less of the kinase activity of wild-type SOK; more preferably, 25% or less; more preferably, 10% or less; and most preferably, 5% or less of the kinase activity of wild-type SOK. One embodiment is a kinase inactive mutant of SOK-1, in which the invariant lysine in the ATP binding site has been substituted with an arginine.

The invention also features a therapeutic composition containing a kinase inactive mutant of a SOK polypeptide, or DNA encoding such a mutant, as an active ingredient. In another aspect, the invention features a method of down-regulating the gene encoding NFκB by administering a therapeutically effective amount of a kinase inactive mutant of a SOK polypeptide, or a DNA encoding such a kinase inactive mutant.

Biologically active fragments of SOK polypeptides, and DNAs encoding such polypeptides, are also included in the invention. An example of such an active fragment is the portion of the SOK-1 polypeptide corresponding to the noncatalytic carboxy terminal region of SOK-1. A "biologically active" fragment is a fragment having at least 10% of the activity of SOK in specific functions, e.g., induction of cell cycle arrest. For example, a biologically active fragment can have 30%, 50%, 80%, 90% or up to 100% or more of the activity of SOK. Such fragments include that encoded by amino acids 286 to 426 of SOK-1, and that encoded by amino acids 286 to 336 of SOK-1.

Therapeutic compositions of the invention include such active fragments, or DNAs encoding such fragments, formulated with a pharmaceutically acceptable carrier. A therapeutically effective amount of such a composition is administered to a patient, e.g., to treat a condition characterized by a proliferative response, such as balloon angioplasty-induced injury, inflammatory responses, or cancer.

Unless otherwise defined, all technical and scientific terms used herein have the same meaning as commonly understood by one of ordinary skill in the art to which the invention pertains. All publications mentioned herein are incorporated by reference. The examples which follow are illustrative only, and not intended to be limiting.

Other advantages and features of the invention will be apparent from the detailed description, and from the claims.

BRIEF DESCRIPTION OF THE DRAWINGS

FIG. 1 is a diagram of the nucleotide and predicted amino acid sequences of human SOK-1.

FIG. 2 is a diagram showing an alignment of the amino acid sequence of the catalytic domain of SOK-1 with the amino acid sequence of the catalytic domains of other Ste20 homologs.

FIGS. 5A–F are immunofluorescent stains of SOK-1-transfected cells, showing the subcellular localization of SOK-1.

FIG. 9B is a diagram showing the effect of SOK-1 on the ERK1 cascade.

DETAILED DESCRIPTION

Figure 3:
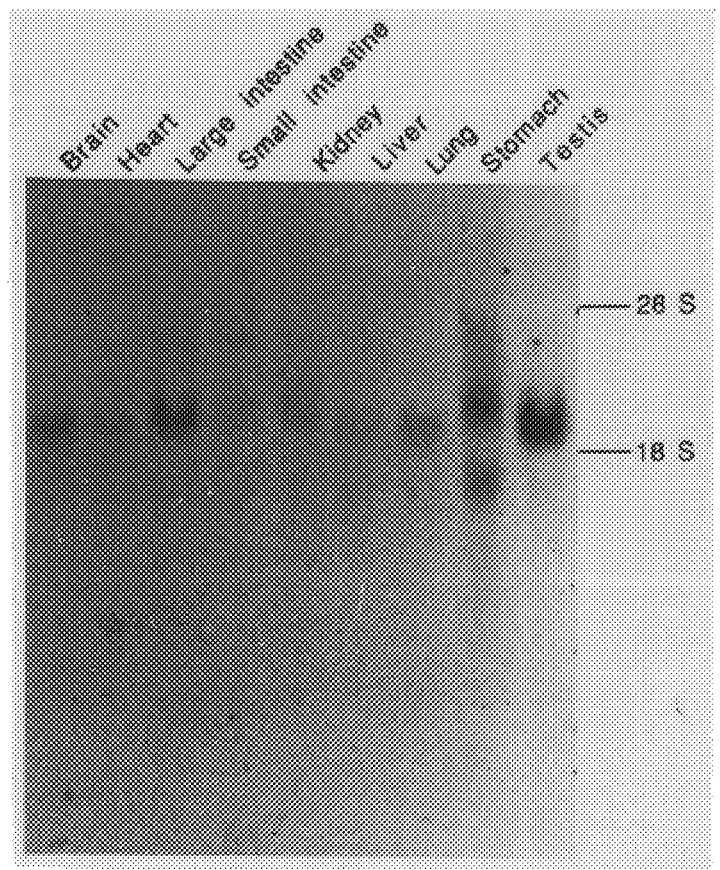
FIG. 3 is an autoradiogram of a northern blot of RNA from various tissues, hybridized to a SOK-1 probe.

Mammalian homologs of the yeast serine/threonine protein kinase, Ste20, can be divided into two groups based on their regulation and structure. The first group, the Ste20 family, includes PAK1 and is regulated by Rac1 and cdc42Hs. Activators of protein kinases in the Ste20 family have been identified. In contrast, little has been known about activators, regulatory mechanisms or physiological roles of the second family, the Sps1 family, which includes GC kinase and MST1. The present invention is based on the identification, cloning and characterization of a human Ste20 homolog, SOK-1. Like members of the Sps1 family of Ste20 homologs, SOK-1 is characterized by an amino terminal catalytic domain. SOK-1 is positively regulated by phosphorylation, and is negatively regulated by its noncatalytic carboxy terminal region. There is no significant sequence similarity between this noncatalytic regulatory region and any other protein kinases.

SOK-1 is markedly activated by depletion of intracellular ATP stores, an important component of ischemia. This novel protein kinase is also activated by oxidant stress, and is the first mammalian Ste20 known to be activated by any cellular stress. This novel protein kinase is not activated by growth factors, alkylating agents, cytokines or environmental stresses including heat shock and osmolar stress. SOK-1 does not act as part of a generalized stress response pathway, but is activated relatively specifically by oxidant stress. Oxidant stress is a prominent component of ischemia and of reperfusion of ischemic tissue.

SOK-1 activates the transcription factor NFκB, which is implicated in a host of pathological conditions including inflammation and autoimmune syndromes. A kinase inactive mutant of SOK-1 can inhibit NFκB activity. SOK-1 also induces cell cycle arrest via a pathway that is independent of other stress activated protein kinases known to effect cell cycle arrest. This cell cycle arrest is mediated by the noncatalytic subunit of SOK-1.

Unlike GC kinase, a member of the Ste20 family, and PAK1, a member of the Sps1 family, SOK-1 does not activate any of the known MAPK pathways, such as SAPK/JNK, p38 or ERK1/-2. SOK-1 thus defines a novel stress response pathway which is likely to include a unique stress-activated MAP kinase cascade. The data suggest that SOK-1 functions similarly to yeast Ste20s, which transduce signals in response to environmental stress.

MATERIALS AND METHODS

Isolation and Analysis of SOK-1 cDNA

Degenerate sense [GA(A/G)(C/T)TIATGGCIGTIAA(A/G)CA] (SEQ IF NO:8) and antisense [TTIGCICC(T/C)TTIAT(A/G)TCIC(G/T)(A/G)TG] (SEQ ID NO:9) primers were used to amplify DNA from a human placenta cDNA library using Taq polymerase. The PCR products were ligated into the PCRII vector (Invitrogen). A 350 bp fragment was obtained which was not in the database but which had significant homology to the catalytic domain of protein serine/threonine kinases. This fragment was used to screen 500,000 plaques from a human B cell cDNA library in λYES (provided by Stephen J. Elledge, Department of Biochemistry, Baylor College of Medicine). Seven positive clones were isolated, and those containing the largest inserts were analyzed by DNA sequencing of both strands using the dideoxy chain termination method with Sequenase 2.0 (USB, Inc.). DNA and amino acid sequence comparisons were made using the University of Wisconsin Genetics Computer Group programs BLAST, Pileup, and Bestfit, and the BEAUTY (BLAST Enhanced Alignment Utility) and BLASTPAT (BLAST PATtern database search tool) programs from the Human Genome Center, Baylor College of Medicine.

Northern Blot Analysis

Total RNA was isolated from rat organs by the guanidinium thiocyanate-phenol-chloroform method (Witzgall et al., *Mol. Cell. Biol.* 13:1933 (1993)). Twenty μg of total RNA was size-fractionated on a 1% formaldehyde-agarose gel and transferred to GeneScreen Plus (NEN) membrane as described. Id. Blots were hybridized with a 409-bp HindIII-BamHI fragment from the 3' half of SOK-1 (nucleotides 995–1403) which included 284 bp of open reading frame encoding part of the non-catalytic region, and 125 bp from the 3' untranslated region. This probe was labelled with $[\alpha]$-$^{32}$p dCTP by random priming. Hybridization was carried out for 18 hours at 45° C. in 5×SSPE (1×SSPE: 150 mM NaCl, 10 mM $NaH_2PO_4$, 0.7 mM EDTA), 44% formamide, 5×Denhardt's solution, 1% SDS, 10% Dextran Sulfate, and 100 μg/ml denatured salmon sperm DNA. The membranes were washed twice for 15 minutes at room temperature in 2×SSPE, twice for 30 minutes at 65° C. in 2×SSPE with 2% SDS, and once for 30 minutes at room temperature in 0.2×SSPE. Membranes were exposed to X-ray film for 5 days at −70° C. with intensifying screens.

Plasmids

Plasmids used included pMT3 (pMT2 modified to include sequence encoding the 9 amino acid hemagglutinin (HA) epitope N-terminal to the insert) (Pombo et al., Nature 377:750 (1995)), pCMVS (a CMV-based vector including sequence encoding the 9 amino acid M2 epitope tag N-terminal to the insert), PEBG (a vector that is driven by the human EF-lα promoter and that includes sequence encoding glutathione s-transferase (GST) N-terminal to the insert) (Pombo et al., Nature 377:750 (1995); Sanchez et al., Nature 372:794 (1994)), and pGEX-KG (a prokaryotic expression vector that includes sequence encoding GST N-terminal to the insert) (Guan et al., Anal. Biochem. 192:262 (1991)).

To create pCMV5-SOK-1ΔC, pCMVS-SOK-1 was cut with HindIII and then religated. The pCMV5-SOK-1ΔC construct contains sequence encoding amino acids 1–333 and includes the entire kinase domain of SOK-1, but not the carboxy terminal 93 amino acids of the protein. pEBG-SAPKpS4β, pEBG-p38, pEBG-ERK1 contain the three MAP kinases p54β (the β isoform of the SAPK, p54), p38, and ERK1, respectively, as GST fusion proteins. pRSV-BXB-Raf-1 encodes a variant of c-Raf-1 lacking the regulatory domain. BXB-Raf-1 is constitutively active and transforming (Bruder et al., Genes & Development 6:545 (1992); Pombo et al., Nature 377:750 (1995); Sanchez et al., Nature 372:794 (1994)).

Transfection Protocols and Kinase Assays

Subconfluent COS7 cells were transfected using the DEAE-dextran technique as described (Pombo et al., Nature 377:750 (1995)). One to ten μg of expression plasmid DNA were used per plate and adjusted to a total of 20 μg of DNA with the appropriate empty vector. Forty-eight hours after transfection, cells were exposed to various stimuli or vehicle, and extracts were prepared as described (Pombo et al., Nature 377:750 (1995); Pombo et al., J. Biol. Chem. 269:26546 (1994)). Extracts were exposed to anti-HA or anti-M2 (Kodak) monoclonal antibodies, or to an anti-SOK-1 rabbit polyclonal antibody (see below) for 3 hours, and immune complexes were collected with Protein G-Sepharose beads. Beads were washed three times in lysis buffer, three times in LiCl buffer (500 mM LiCl, 100 mM Tris-HCl, pH 7.61, and three times in assay buffer (Pombo et al., J. Biol. Chem. 269:26546 (1994)). Kinase assays were started by the addition of myelin basic protein (MBP, for SOK-1 and ERK1); GST-c-Jun (1–135), containing the transactivation domain of c-Jun (for SAPK) (Kyriakis et al., Nature 369:156 (1994); Pombo et al., Nature 377:750 (1995); Pombo et al., J. Biol. Chem. 269:26546 (1994)); or ATF-2 (8–94), containing the transactivation domain of ATF-2 (for p38) (Morooka et al., J. Biol. Chem. 270:30084 (1995)), in the presence of $[\gamma]$-$^{32}$P-ATP (100 μM, 3000–9000 cpm/pmole) and MgCl$_2$ (10 mM) After 5 to 20 minutes at 30° C., the kinase reactions were stopped with Laemmli sample buffer. Following SDS-polyacrylamide gel electrophoresis and autoradiography, the bands corresponding to the substrate were cut out of the gel and radioactivity was determined by liquid scintillation counting. For all kinase assays, an aliquot of the cell lysate was run on an SDS-polyacrylamide gel, transferred to Imobilon, and subjected to immunoblotting with the appropriate antibody to ensure equivalent expression of the kinases (Morooka et al., J. Biol. Chem. 270:30084 (1995)). Antibody binding was detected using the Enhanced Chemiluminescence System.

Phosphatase Inactivation and Reactivation Experiments

Six 10 cm dishes of COS7 cells were transfected with pMT3-SOK-1. Forty eight hours later, cell lysates were subjected to immunoprecipitation with anti-HA antibody. Immune complexes were divided into equal aliquots and then incubated for 20 minutes at 30° C. with the catalytic subunit of protein phosphatase 2A (PP2A), either with or without the PP2A inhibitor, okadaic acid (100 nM). PP2A was purified from rabbit skeletal muscle (Chen et al., Science 257:1261 (1992)) and was generously provided by Dr. David Brautigan (Center for Cell Signalling, University of Virginia Health Science Center). After the 20 minute incubation, okadaic acid was added to bring the final concentration to 100 nM in all tubes. Immune complexes were washed twice with kinase assay buffer, and then exposed to $[\gamma]$-$^{32}$P-ATP (100 μM) for 0, 5, 10, or 20 minutes prior to the addition of MBP and subsequent kinase assay for 5 minutes at 30° C.

Production of Anti-SOK-1 Polyclonal Antibodies

A peptide (amino acids 333–426) from the non-catalytic region of SOK-1 was used to generate a polyclonal rabbit antibody. This peptide was expressed in bacteria from pGEX-KG as a GST fusion protein, purified, and used to immunize rabbits according to standard protocols (Harlow et al., Antibodies: A Laboratory Manual, Cold Spring Harbor Laboratory, Cold Spring Harbor, N.Y. (1988)). The antibodies from each of two rabbits recognized 1 ng of GST-SOK1 on a Western blot when used at a 1:1000 dilution. In addition, at a 1:250 dilution, the antibody immunoprecipitated HA-SOK-1 from lysates of transfected cells.

Production of Anti-SOK-1 Monoclonal Antibodies

Monoclonal antibodies can be generated using the standard Kohler and Milstein technique.

Microinjection and Immunofluorescence

Mouse fibroblast NIH 3T3 cells were grown on glass coverslips and microinjected with the pMT3-SOK-1 expression vector, encoding SOK-1 with the HA epitope tag at its amino terminus. Plasmid DNA was purified twice on a CsCl gradient and extracted three times with phenol and chloroform. Cells were injected in a 3.5 cm dish with an automated microinjection system (AIS; Zeiss (Ansorge et al., J. Biochem Biophys. Meth. 16:283 (1988)) at a pressure between 80 and 170 kPa. The computer settings were as follows: angle, 45°; speed, 10; and time, 0.0 sec. Plasmid DNA was injected at a concentration of 100 μg/ml concentration (Pagano, Genes & Development 8:1627 (1994)). Twenty-four hours after injection, the cells were fixed with 4% paraformaldehyde for 15 minutes, treated with 0.1% SDS in phosphate buffered saline (PBS) for 5 minutes, and permeabilized with 0.5% Triton X100 (in PBS) for 15 minutes. Cells were then processed for immunofluorescence (Brown et al., J. Histochem. Cell. Biol., in press, 1996).

All antibodies were diluted in Dulbecco's modified Eagle's medium containing 10% calf serum. Coverslips were incubated with affinity purified anti-HA antibody (Boehringer Mannheim) at a final concentration of 0.026 mg/ml for one hour. After incubation for 40 minutes in biotinylated goat anti-mouse antibody (Jackson Laboratories) which was diluted 1:50, the coverslips were incubated for 40 minutes in fluorescein isothiocyanate conjugated streptavidin, diluted 1:100 (Jackson Laboratories). All incubations were carried out at 37° C. in a humidified chamber. Between each step, cells were washed three times with PBS. Nuclei were counterstained with bisbenzimide (Hoescht 33258) for 2 minutes at 1 mg/ml in PBS. Coverslips were mounted in Crystal/Mount (Biomedia) and visualized on a Zeiss Axiovert 100 photomicroscope. Cells were imaged with a Bio-Rad Laser Scanning Confocal Microscope.

Derivation of SOK-1 Kinase Inactive Mutants

A kinase inactive mutant of SOK-1 was derived by mutating the ATP binding site of SOK-1, by replacing the invariant lysine with arginine.

Identification and Characterization of SOK-1, A Novel Ste20 Homolog

Screening of the human B cell cDNA library identified two clones of 1.8 kb and 2.0 kb. The nucleotide sequence of the gene encoded by these overlapping clones, and the deduced amino acid sequence of the protein encoded by this gene, are shown in FIG. 1. For the nucleotide sequence, numbers refer to the position of the codon relative to the initiator ATG. The predicted translation product is indicated below the nucleotide sequence, and the numbers refer to the position of the amino acid relative to the initial methionine. The 2.0 kb clone contains a Kozak sequence (gcggccatgg) (SEQ ID NO:10) at a candidate initiation codon (FIG. 1). There is an in-frame stop codon 15 bp 5' of this initiation codon. There are no other candidate initiation codons between this stop codon and the ATG, which suggests that this codon is the true translation start site. A poly (A) tail is present at the 3' end of the 1.8 kb clones.

The open reading frame encodes a protein which is 426 amino acids in length and has a predicted molecular mass of 48,041 daltons. The kinase domain is located in the amino terminal half of the protein and contains all 11 subdomains of serine/threonine kinases (Hanks et al., In *Methods in Enzymology*, Hunter et al., eds., Academic Press, San Diego, Calif., pp. 38–62 (1991)). Alignment of the catalytic domain of SOK-1 with the catalytic domains of the five most closely related kinases as determined by the BLAST and Bestfit programs is shown in FIG. 2. The deduced amino acid sequences of PAK1 (Manser et al., *Nature* 367:40 (1994)); Ste20 (Leberer et al., *EMBO J.* 11:4815 (1993)); MST1 (Creasy et al., *J. Biol. Chem.* 270:21695 (1995)); Sps1 (Friesen et al., *Genes & Development* 8:2162 (1994)); and GC kinase (Katz et al., *J. Biol. Chem.* 269:16802 (1994)) were aligned by eye after being aligned with the Pileup program. Gaps, which were introduced to maintain alignment, are denoted by dots. Roman numerals indicate the eleven protein serine/threonine kinase subdomains (Hanks et al., In *Methods of Enzymology*, Hunter et al., eds., pp. 38–62, Academic Press, Inc., San Diego, Calif. (1991)). Residues that are conserved in all family members are enclosed in boxes. Comparison of the amino acid sequence of the catalytic domain with other protein kinases using the BLAST program identified the yeast kinase, Sps1 (Friesen et al., *Genes & Development* 8:2162 (1994)), and the mammalian kinases, MST1 (Creasy et al., *J. Biol. Chem.* 270:21695 (1995)) and GC kinase (Katz et al., *J. Biol. Chem.* 269:16802 (1994)) as its closest homologs. Within the catalytic domain, SOK-1 was 50% identical and 68% similar to Sps1, 56% identical and 73% similar to MST1, and 51% identical and 68% similar to GC kinase.

The five kinases most closely related to SOK-1 are Sps1, MST1, GC kinase, Ste20 (Leberer et al., *EMBO J.* 11:4815 (1993)), and PAK1 (Manser et al., *Nature* 367:40 (1994)), all of which are Ste20 homologs. Alignment of the amino acid sequence of the catalytic domains of Sps1 and Ste20 with SOK-1 indicates a high degree of evolutionary conservation (FIG. 2). Comparison of the amino acid sequence of the C-terminal non-catalytic region of SOK-1 with the database using the BLAST, BEAUTY, and BLASTPAT programs failed to identify regions of significant homology with any other kinases.

SOK-1 is thus related to the Sps1 family of Ste20s on the basis of its organization, i.e., amino terminal catalytic domain, and sequence similarity within the kinase domain to the Sps1 group. SOK-1 is more similar in sequence to Sps1 (50% identical) than it is to Ste20 (42% identical). Furthermore, Sps1 is more similar to SOK-1 than Sps1 is to Ste20 (44% identical).

SOK-1 Expression mRNA was extracted from various rat tissues and subjected to Northern blot analysis using a probe from the carboxy terminal non-catalytic region of SOK-1. Expression of a 2300 bp mRNA was detected in all tissues examined except stomach, where the probe hybridized to two transcripts, one of approximately 2600 bp and one of 1500 bp (FIG. 3). Highest levels of expression were in testis, large intestine, brain, and stomach. Intermediate levels of expression were seen in heart and lung. Equal loading of all lanes in the gel was confirmed by ethidium bromide staining. The kinase was expressed in the two human B cell lines examined, Ramos, a Burkitt lymphoma cell line that has features of a germinal center B cell, and HS Sultan, a mature B cell line.

Figure 4A:
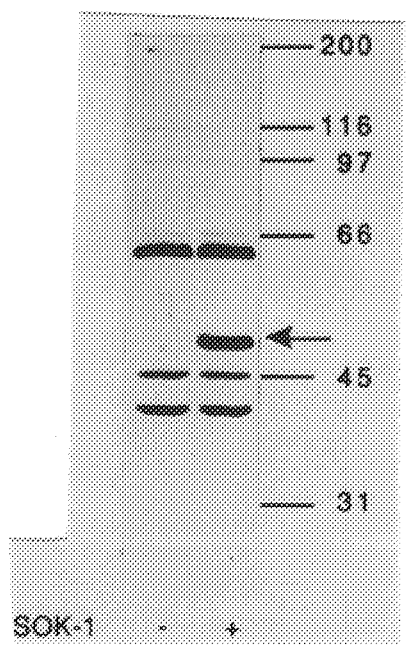
FIG. 4A is an autoradiogram of a western blot of cells transfected with a HA epitope tagged-SOK-1 gene, probed with anti-HA antibody.
Figure 4B:
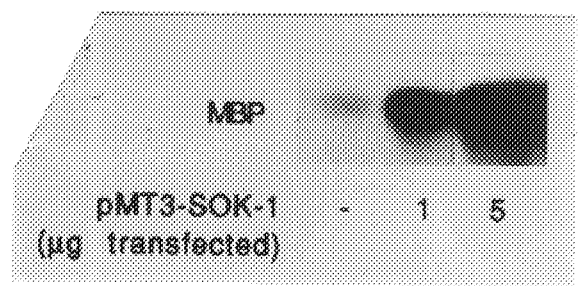
FIG. 4B is an autoradiogram of cells transfected with a HA epitope-tagged SOK-1 and immunoprecipitated with anti-HA antibody, followed by immune complex kinase assay using MBP as substrate.

COS7 cells were transfected with pMT3-SOK-1, which encodes a SOK-1 protein with a nine amino acid HA epitope tag on the amino terminus. The results of Western blotting using a monoclonal anti-HA antibody as a probe of the pMT-3SOK-1 transfected cells (+), as well as cells transfected with the vector without the SOK-1 insert (−) are shown in FIG. 4A. Transfection with pMT3-SOK-1, but not the vector alone, resulted in expression of a protein with an approximate molecular weight of 50 kDa (indicated by the arrow in FIG. 4A). The kinase displayed a high degree of constitutive activity toward MBP in immune complex kinase assays. The results of a typical experiment in which COS7 cells were transfected with pMT3 vector alone (−), or 1 μg (1) or 5 μg (5) pMT3-SOK-1 is shown in FIG. 4B. Forty eight hours after transfection, the cells were harvested and lysates were subjected to immunoprecipitation with anti-HA antibody followed by immune complex assay using MBP as substrate. Phosphoamino acid analysis demonstrated that the kinase phosphorylated MBP on serine and threonine residues, but not on tyrosine.

To determine subcellular localization of SOK-1, pMT3-SOK-1, encoding HA-SOK-1, was microinjected into NIH3T3 fibroblasts at a concentration of 100 μg/ml. HA-SOK-1 was detected by staining with the anti-HA antibody as described supra. SOK-1 was localized almost exclusively in the cytoplasm (FIGS. 5B and 5E). A representative slice of 0.2 μm of the same cells is also shown in FIGS. 5A and 5D. The cells were counterstained with Hoescht 33258 to visualize the nuclei (FIGS. 5C and 5F).

Regulation of SOK-1

Figure 6:
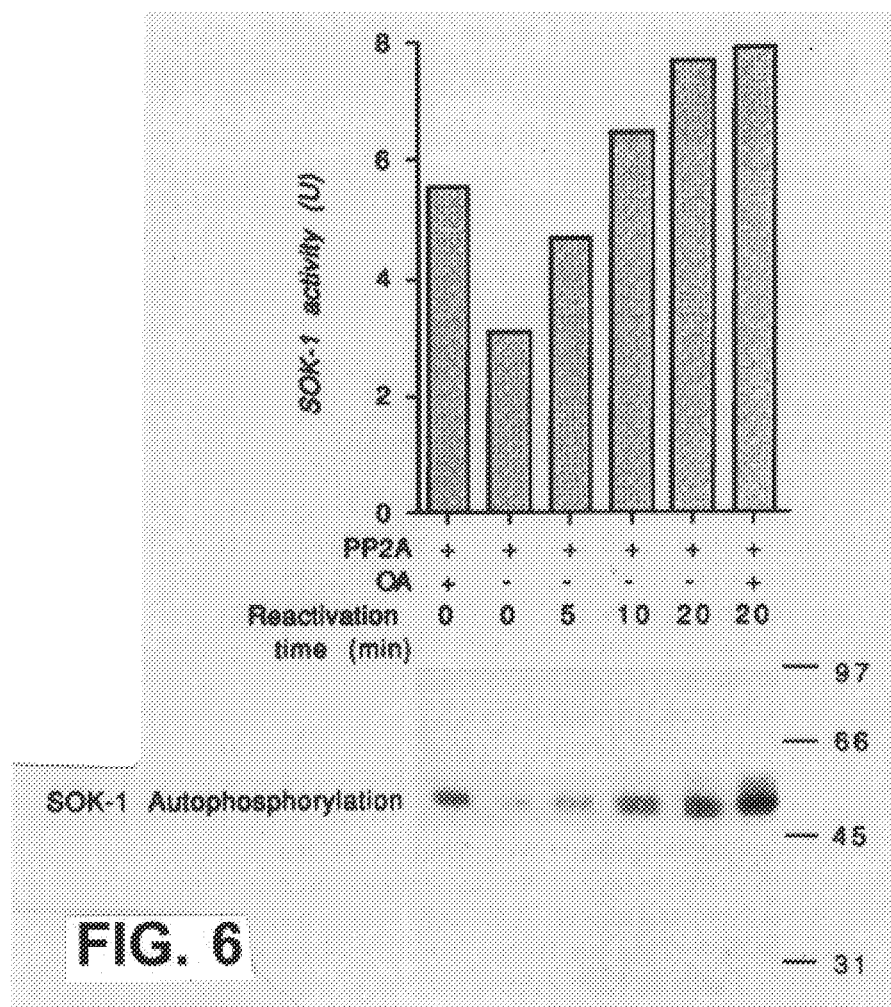
FIG. 6 is a diagram showing the effect of Protein Phosphatase 2A (PP2A) and autophosphorylation on SOK activity.

The role of phosphorylation in the regulation of SOK-1 was explored. Exposure of SOK-1 to protein serine phosphatase 2A (PP2A) in immune complexes reduced SOK-1 kinase activity by approximately 40%. This effect of PP2A was prevented by co-incubation with the PP2A inhibitor okadaic acid (OA). To determine whether autophosphorylation might play a role in activating SOK-1, the protein was partially inactivated by PP2A, then incubated with $\gamma$-$^{32}$P-ATP (100 μM) and assayed for reactivation (FIG. 6). Reactivation of SOK-1 kinase activity which correlated with phosphorylation of a 50 kDa protein in the immune complex. The increase in kinase activity over time correlated with the degree of phosphorylation. The phosphorylated protein also demonstrated enhanced electrophoretic mobility after PP2A treatment and retarded mobility after incubation with ATP (FIG. 6). The data thus suggest that phosphorylation, probably autophosphorylation, is an important mechanism of activation of SOK-1.

Autophosphorylation and autoactivation of a kinase in immune complexes, if unrecognized, greatly complicates the identification of activators. After a twenty minute incubation in the presence of ATP, MBP kinase activity of SOK-1 previously inactivated by PP2A, was equal to that of SOK-1 which had not been inactivated by PP2A (FIG. 6). Autophosphorylation and autoactivation may explain the difficulty which has been encountered in identifying activators of the Sps1 family of Ste20 homologs when standard immune complex kinase assays are performed. Under these conditions, no activators of MST1 were identified (Creasy et al., *J. Biol. Chem.* 270:21695 (1995)), and for GC kinase, TNFA only weakly stimulated kinase activity. Since SOK-1 is markedly activated by autophosphorylation in immune complex kinase assays, incubations for kinase assays of longer than 5 minutes can be expected to mask any differences between control and stimulated cells. Consequently, all subsequent kinase assays were performed for 5 minutes.

Figure 7:
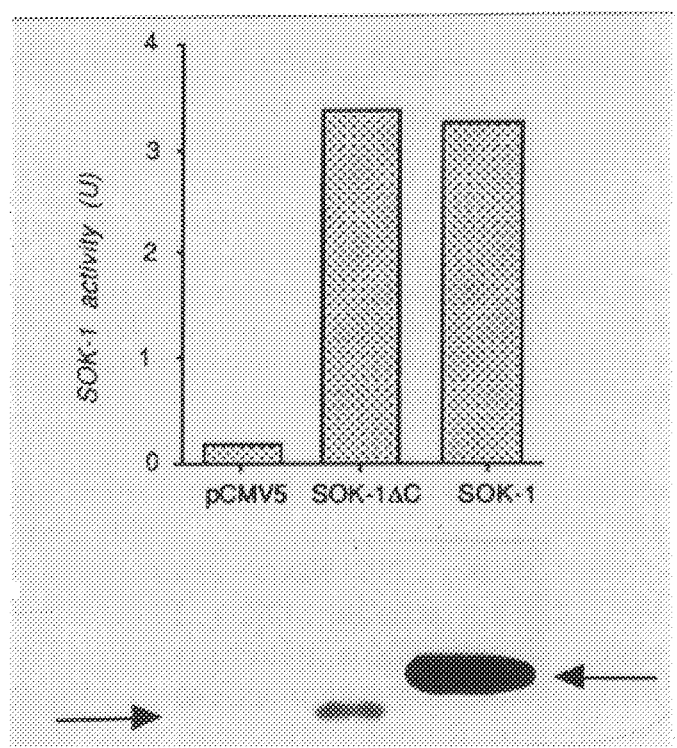
FIG. 7 is a diagram showing the effect of the C-terminal non-catalytic region on SOK-1 kinase activity.

SOK-1 has an amino terminal catalytic domain, placing it, on the basis of organization, in the Sps1 group of Ste20s, which includes Sps1, GC kinase, and MST1. These kinases lack the Rac1/cdc42Hs binding domain present in the regulatory domains of Ste20 and the PAK family of kinases, and the role of their carboxy terminal non-catalytic regions is unclear. The ability of the carboxy terminal region of SOK-1 to regulate kinase activity in transfected COS7 cells was tested (FIG. 7). Using MBP as a substrate, the kinase activity of SOK-1, expressed from pCMV5-SOK-1, which encodes SOK-1 with a nine amino acid M2 epitope tag at the amino terminus, was compared with that of M2-SOK-1ΔC, a deletion mutant containing the catalytic domain but missing the carboxy terminal 95 amino acids of the non-catalytic region, and pCMV5, which is the vector containing the M2 epitope tag, but lacking the SOK-1 sequences. Although the cellular extracts were matched for total protein prior to immunoprecipitation with anti-M2 antibody, immunoblots of the extracts revealed that M2-SOK-1ΔC was expressed at a much lower level than full-length M2-SOK-1 (FIG. 7, bottom). Despite the lower expression of M2-SOK-1ΔC, and the presence of much less M2-SOK-1ΔC compared to full-length M2-SOK-1 in the immunoprecipitates, kinase activity, measured as phosphorylation of MBP, was equivalent, consistent with significantly greater specific activity of M2-SOK-1ΔC (FIG. 7). These data suggest that the carboxy terminal non-catalytic region inhibits kinase activity of SOK-1 and is the first demonstration of a role for the non-catalytic region of protein kinases related to the Sps1 group of Ste20s. Inhibition of activity may be due to binding of the carboxy terminal region to the catalytic domain, since the carboxy terminal region (lacking the kinase domain) co-immunoprecipitates with SOK-1ΔC when the two are co-expressed. The carboxy terminal region may exert its inhibitory effect by preventing access by an activator, possibly SOK-1 itself, to a critical site within the catalytic domain, or by inhibiting interaction of the kinase domain with substrates.

SOK-1 is thus regulated by its non-catalytic region, and by phosphorylation. Identification of these two regulatory mechanisms suggests that the regulation of SOK-1 may be similar to the regulation of PAK1. Binding of the inhibitory regulatory region of PAK1 to the small GTP binding proteins appears to allow the kinase to undergo autophosphorylation, which activates the kinase. For SOK-1, binding of the inhibitory regulatory region to an as yet unidentified activator may also allow autophosphorylation and activation to occur. Thus, the primary mechanism of activation of PAK1 and SOK-1 (and possibly other Ste20s) would be similar (autophosphorylation), but the activators to which the regulatory domains bind, allowing autophosphorylation to occur, would differ. Specificity in the activation of Ste20s (and subsequently, MAP kinase cascades) in response to a stimulus could be determined by protein or lipid interaction domains within the regulatory region.

Activation of SOK-1 by Depletion of ATP Stores

SOK-1 is markedly activated by the depletion of intracellular ATP stores, an important component of ischemia. Ischemia is a major cause of morbidity and mortality, and clinically presents as myocardial infarction, stroke, and acute renal failure. Several kinases are activated after reperfusion or after repletion of ATP stores, but SOK-1 is activated during the phase of ATP depletion, suggesting that it is a very early modulator of the response to ATP depletion and therefore ischemia.

Activation of SOK-1 by $H_2O_2$

Figure 8:
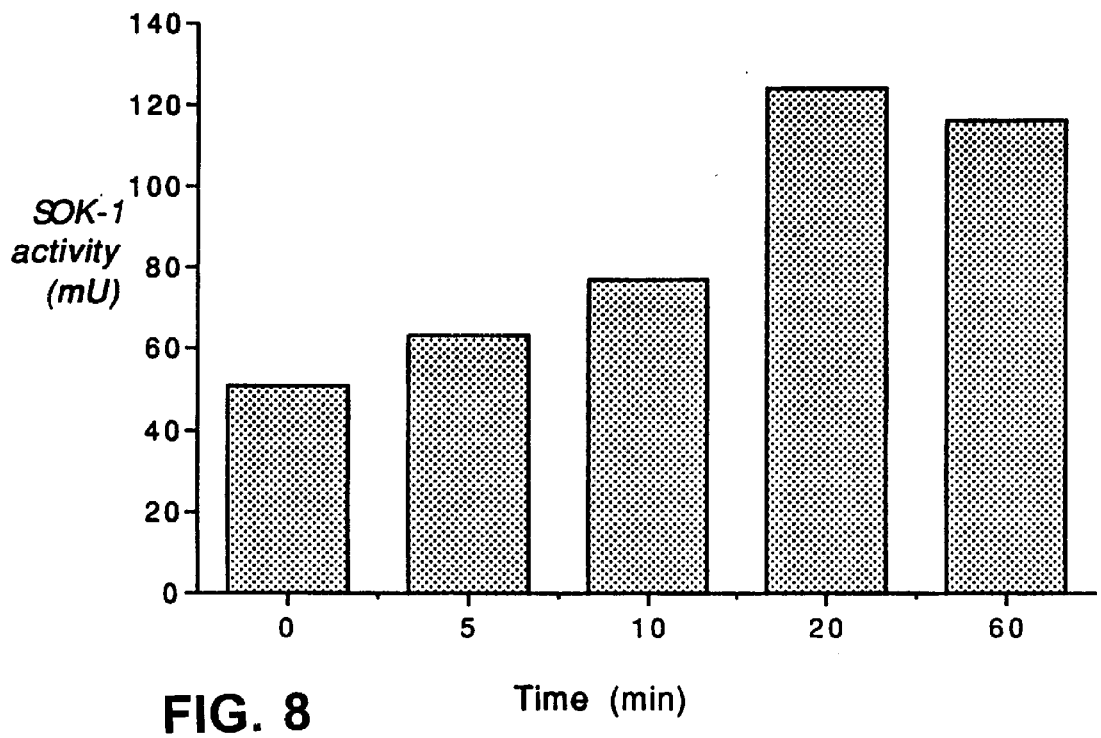
FIG. 8 is a diagram showing the kinetics of activation of SOK-1 by $H_2O_2$.

Incubation of Ramos B cells with okadaic acid (1 μM, 20 minutes) activated SOK-1 (Table 1), compatible with regulation of SOK-1 (and/or an upstream activator) by phosphorylation. Numerous agonists that were representative of multiple different classes of stimuli were also tested for their ability to activate SOK-1. Only $H_2O_2$ consistently activated SOK-1 when native kinase was assayed after immunoprecipitation from Ramos B cells or when HA-tagged SOK-1 was assayed after immunoprecipitation from transfected COS7 cells (Table 1). $H_2O_2$ (0.5 mM) activated SOK-1 approximately 3-fold ($p<0.01$). No $H_2O_2$-induced increase in MBP kinase activity was detected when immunoprecipitation was performed with preimmune serum. Activation of SOK-1 was evident as early as 10 minutes following exposure of Ramos B cells to $H_2O_2$, peaked at 20 minutes, and remained elevated at 60 minutes (FIG. 8). Activation was evident at 0.1 mM, the lowest concentration tested (2.1-fold increase in kinase activity). SOK-1 is thus markedly activated by oxidant stress. Oxidant stress is a prominent component of ischemia, and of reperfusion of ischemic tissue. Oxidant stress also occurs with ionizing radiation, such as ultraviolet or gamma radiation, and is an important element of inflammation.

This is the first clear demonstration of activation of a member of this group of Ste20s by any stimulus. The activation of SOK-1 by $H_2O_2$ not only identifies a new oxidant stress response signal transduction pathway, but also suggests that one role of this and possibly other Ste20s of this group is to respond to environmental stresses just as their homologs do in the simplest eukaryotes. The survival of aerobic organisms depends upon their mounting an effective response to oxidant stress. Activation by oxidant stress suggests that SOK-1, and possibly other as yet unidentified SOK-1 homologs, may, like the Ste20s identified thus far in yeast, play an important role in the responses of the cell to environmental stress.

In contrast to activation of SOK-1 by $H_2O_{21}$ potent activators of the ERK1/-2 cascade, such as epidermal growth factor (EGF), platelet-derived growth factor (PDGF) and the phorbol ester phorbol myristate acetate (PMA) combined with the calcium ionophore, ionomycin, did not activate SOK-1 (Table 1). In the same COS7 cells, these agonists activated ERK1, expressed in pEBG, 5- to 7-fold. Oxidant stress appeared to be a specific activator among the several cellular stresses tested. Specifically, high and low osmolar stress, heat shock, tumor necrosis factor α (TNFα), and anisomycin, which potently activate the SAPK and/or p38 cascades in these and other cells (see Figs. and Galcheva-Gargova et al., Science 265:806 (1994); Han et al., Science 265:808 (1994); Kyriakis et al., Nature 369:156 (1994); Pombo et al., Nature 377:750 (1995); Rouse et al., Cell 78:1027 (1994)), did not activate SOK-1. Platelet activating factor, which signals via a heterotrimeric G protein-coupled receptor and is a potent activator of intracellular $Ca^{2+}$ transients in Ramos cells, was also ineffective.

TABLE 1

Fold-activation of native SOK-1 in Ramos B cells and HA-SOK-1 in COS7 cells.

| Agonist | Ramos | COS7 |
| --- | --- | --- |
| $H_2O_2$ (0.5 mM, 20 min) | 2.9 | 2.8 |
| Okadaic acid (1 μM, 30 min) | 2.3 | — |
| Interferon-γ (50 ng/ml, 20 min) | 1.0 | — |
| TNFα (50 ng/ml, 20 min) | 1.5 | 0.9 |
| Anti-Ig (20 min) | 0.8 | — |
| Platelet activating factor (1 μM, 20 min) | 1.4 | — |
| PMA/Ionomycin (300 nM/1 μM, 20 min) | 1.4 | 1.4 |
| Nitrogen mustard (10 μM, 30 min) | 1.2 | 1.4 |
| Cyclophosphamide (10 μM, 30 min) | 0.9 | 1.5 |
| cisplatin (10 μM, 30 min) | 1.0 | 1.1 |
| Heat shock (42° C., 5 min) | — | 0.9 |
| Anisomycin (50 μg/ml, 20 min) | — | 1.1 |
| Hyperosmolarity (NaCl 700 mM, 15 min) | — | 0.9 |
| Hypoosmolarity (150 mOsm, 15 min) | — | 0.9 |
| EGF (100 ng/ml, 10 min) | — | 1.3 |
| PDGF (20 ng/ml, 10 min) | 1.0 | 1.2 |

— = not determined.

Native SOK-1 in Ramos B cells was assayed with MBP as substrate after immunoprecipitation with rabbit polyclonal anti-SOK-1. HA-SOK-1 was assayed after immunoprecipitation with anti-HA antibody from extracts of COS7 cells which had been transfected with pMT3-SOK-1 (5 μg per 10 cm dish).

Hypoosmolar stress was induced by placing cells in Krebs-Henseleit buffer without NaCl (Pombo et al., 1994).

Reactive oxygen radicals, via damage to many cellular components including DNA, can cause cell death, or if less severe, cell cycle arrest at either the $G_1$ or $G_2$ checkpoint (Russo et al., J. Biol. Chem. 270:29386 (1995)). DNA damage not only activates checkpoint controls, but may also activate protein kinases, including the SAPKs, c-Raf-1, and ERKs, which are integral components of cytoplasmic signal transduction cascades, as well as the non-receptor tyrosine kinase c-abl (Hibi et al., Genes & Development 7:2135 (1993); Kharbanda et al., Nature 376:785 (1995); Kharbanda et al., J. Biol. Chem. 270:18871 (1995); Livingstone et al., EMBO J. 14:1785 (1995); Radler-Pohl et al., EMBO J. 12:1005 (1993); Russo et al., J. Biol. Chem. 270:29386 (1995); Van Dam et al., EMBO J. 14:1798 (1995)). In order to determine whether activation of SOK-1 was likely to be triggered by DNA damage or by oxidant stress acting via a DNA damage-independent mechanism, alkylating agents were tested for their ability to activate SOK-1. Alkylating agents activate the DNA damage-induced checkpoint controls and protein kinases, but do not produce oxidant stress. Exposure of transfected COS7 cells to the alkylating agents cyclophosphamide, nitrogen mustard, and cisplatin did not activate SOK-1, suggesting that oxidant stress-induced activation of SOK-1 is not mediated by DNA damage response pathways. Thus, activation of SOK-1 by oxidant stress is not part of a generalized response to either cellular or genotoxic stress. Cross-linking surface IgM on Ramos B cells with anti-Ig antibody coupled to beads, which induces apoptosis in these cells, did not activate SOK-1 but did markedly enhance tyrosine phosphorylation of several proteins in these cells.

Although these data clearly place SOK-1 on an oxidant stress response pathway, SOK-1 does not appear to activate the known stress-activated MAP kinase pathways. It has recently been reported that SOK-1 (previously called UK1; the name was changed to SOK-1 to reflect the fact that the kinase is activated by oxidant stress), unlike the closely related GC kinase, did not activate the SAPKs in co-transfection experiments (Pombo et al., Nature 377:750 (1995)). Co-transfection of HA-SOK-1 with the other MAP kinases, p38 (FIG. 9A) and ERK1 (FIG. 9B), both expressed in PEBG, did not result in the activation of the MAP kinases. In the p38 experiments, COS7 cells were transfected with PEBG vector (p38−) or PEBG encoding p38 as a GST fusion protein (p38+), and either pMT3 vector (SOK-1−) or pMT3 encoding HA tagged SOK-1 (SOK-1+). To confirm that p38 could be activated, cells were exposed to NaCl (500 mM) for 10 minutes (^NaCl+). p38 kinase activity was assayed with ATF-2 (8-94) as substrate (Morooka et al., J. Biol. Chem. 270:30084 (1995)). p38 was markedly activated by exposure of cells to osmolar stress.

In the ERK1 experiments, COS7 cells were transfected with PEBG vector (ERK1−) or pEBG encoding ERK1 as a GST fusion protein (ERK1+), and either pMT3 vector (SOK-1-), pMT3 encoding HA-tagged SOK-1 (SOK-1+), or as a positive control, pMT3 encoding BXB-Raf (+), a constitutively active c-Raf-1 that is missing the amino terminal regulatory domain (Bruder et al., Genes & Development 6:545 (1992)). ERK1 assays were performed in duplicate with MBP as substrate. As shown in FIG. 9B, ERK1 was activated by co-transfection of pRSV-BXB-Raf-1, but not SOK-1.

Figure 9A:
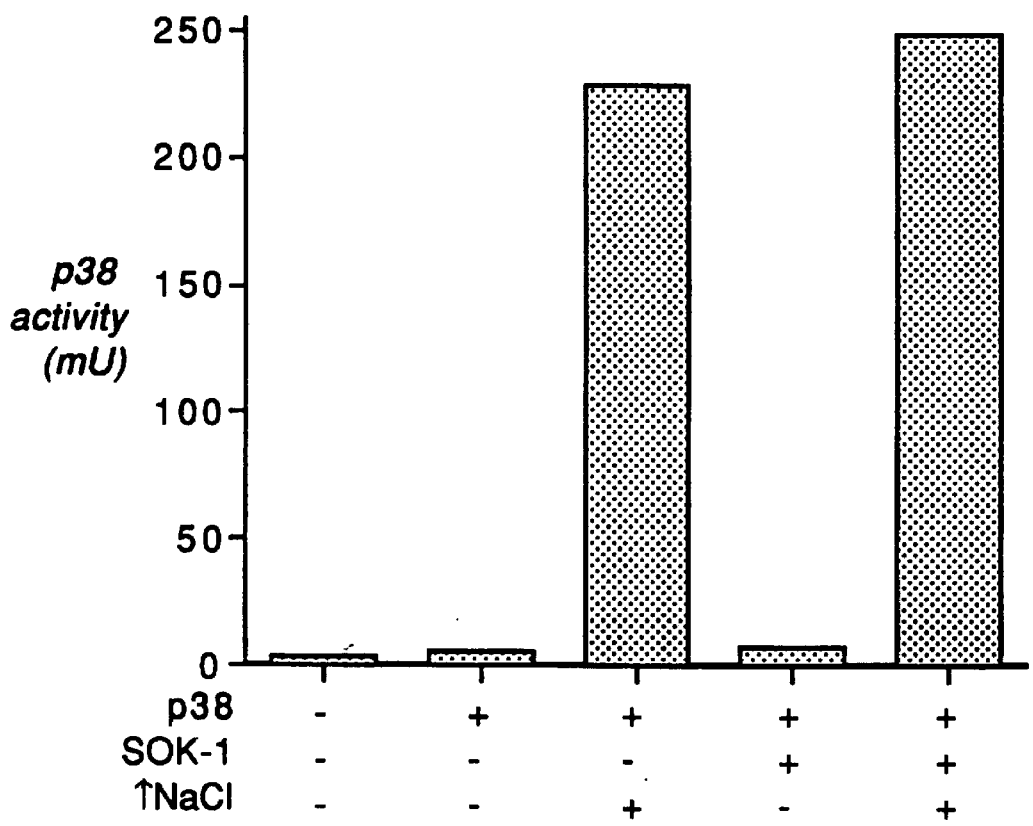
FIG. 9A is a diagram showing the effect of SOK-1 on the p38 cascade.

Oxidant stress activates the ERKs, and may activate the SAPKs somewhat (Kyriakis et al., Nature 369:156 (1994); Russo et al., J. Biol. Chem. 270:29386 (1995)), but SOK-1 does not appear to be implicated in this activation. SOK-1 did not activate any of four MAP kinase cascades, including SAPKs (Pombo et al., Nature 377:750 (1995)); p38 (FIG. 9A); ERK1 (FIG. 9B); or MEK5/ERK5 (Zhou et al., J. Biol. Chem. 270:12665 (1995)), further indicating that the stress response pathway regulated by SOK-1 is unique. Since evolutionary conservation of the activation of MEKK/MEK/MAPK cascades by Ste20s extends to mammals (Polverino et al., J. Biol. Chem. 270:26067 (1995)); Pombo et al., Nature 377:750 (1995); Zhang et al., J. Biol. Chem. 270:12665 (1995)), and all Ste20s identified to date in yeast or mammals, with the exception of MST1 (Creasy et al., J. Biol. Chem. 270:21695 (1995)) have been shown to activate one or more MAP kinase cascades, it is likely that SOK-1 controls a novel oxidant stress-activated MAP kinase cascade.

SOK-1 Functions

NFκB is a ubiquitously expressed transcription factor that is believed to be critical to diverse processes including T lymphocyte activation, the expression of cellular adhesion molecules, and the expression of interferon β. NFκB appears to play vital roles in transplant rejection, post-ischemic injury, the response to viral infection, and inflammation. Many diverse genes are believed to be under the control of NFκB. NFκB is activated by cytokines, such as TNFα, IL-1β, and IL-2; lipopolysaccharide, the mediator of septic shock; viruses, including Human T Cell Leukemia Virus Type 1, Human Immunodeficiency Virus 1, and Hepatitis B; ultraviolet and X-irradiation; antigen stimulation of T and B lymphocyte receptors; and the tumor promoting phorbol esters. In addition, most, if not all, of the activators of NFκB result in oxidant stress. Therefore, SOK-1 could be a final common pathway for activation of NFκB, and SOK-1 having an inactive kinase domain could be a general inhibitor of NFκB. In order to test these hypotheses, reporter plasmids containing NFκB binding sites linked to the Interleukin 2 (IL-2) receptor α-chain promoter were constructed. SOK-1 activated IL-2 receptor α-chain expression from these constructs, indicating that SOK-1 activates NFκB. In addition, transfection of SOK-1 causes an increase in the binding of a nuclear protein to an oligonucleotide containing a consensus NFκB binding site.

A kinase inactive mutant of SOK-1 was constructed by changing the invariant lysine in the ATP binding site to an arginine. This kinase inactive mutant suppresses nuclear protein binding to the oligonucleotide containing the NFκB consensus binding site. Transcription from the NFκB reporter plasmid is also inhibited by the mutant protein. The kinase inactive mutant thus serves as a dominant inhibitor of activation of NFκB. Inhibitors of NFκB have not heretofore been identified, although they have been sought extensively, since it is believed that inhibition or stimulation of NFκB in inflammatory and autoimmune diseases, as well as cancer or viral infection, may be palliative or curative. Verma et al., *Genes & Development* 9:2723 (1995).

SOK-1 and Cell Cycle Arrest

Experiments were performed to investigate the role of SOK-1 in the induction of cell cycle arrest, which occurs in many types of cells following oxidant stress. In these experiments, NIH3T3 cells on coverslips were synchronized in $G_o$ by serum withdrawal. After twenty-four hours, less than 1% of the cells continued to cycle. Arrested cells were released with 10% calf serum, and were microinjected in early $G_1$ phase with the pCMV5 vector alone, or pCMV5 containing the gene encoding M2 epitope-tagged SOK-1. Entry into S phase was determined by monitoring BrdU (0.1 mM) incorporation. After microinjection of the pCMV5 vector alone, over 90% of cells entered S phase. In contrast, after injection of pCMV5-SOK-1, less than 5% of cells entered S phase. Injection of a kinase inactive mutant of SOK-1 also induced cell cycle arrest (<5% of cells in S phase).

Since both SOK-1 and the kinase inactive mutant were effective in maintaining cells in $G_1$, the non-catalytic carboxy terminal region of the kinase might be mediating cell cycle arrest. To test this hypothesis, pCMV5 containing only the non-catalytic region (nucleotides 858 to 1278, encoding amino acids 286 to 426) of the SOK-1 gene was injected into NIH3T3 cells. Like the constructs containing the full length SOK-1 or the kinase inactive mutant, this construct also induced $G_1$ arrest (<5% of cells in S phase) SOK-1 thus potently induces arrest in $G_1$ of the cell cycle, via a mechanism that is not dependent upon the protein's catalytic function. A fragment of the SOK-1 polypeptide of approximately forty amino acids, from amino acid 286 to 336, may be sufficient to induce cell cycle arrest.

SOK-1-mediated cell cycle arrest occurs independently of the p38 and other MAP kinases that are known to induce cell cycle arrest. The ability of SOK-1 to induce cell cycle arrest, as well as to activate NFκB, makes SOK-1 an ideal target for drug development. The ability of SOK-1 to cause cell cycle arrest also suggests that it could be used following balloon angioplasty-induced injury of blood vessels, in order to inhibit the proliferative response which accompanies such injuries and causes restenosis. SOK-1 can also be used to treat other conditions that are characterized by proliferative responses, including inflammatory responses, tumors, and conditions such as atherosclerosis.

Transgenic Animals

SOK polypeptides can also be expressed in transgenic animals. SOK transgenic animals are useful for screening for compounds that enhance or down regulate SOK expression or activity. Animals of any species, including, but not limited to, mice, rats, rabbits, guinea pigs, pigs, micro-pigs, goats, and non-human primates, e.g., baboons, monkeys, and chimpanzees, can be used to generate SOK expressing transgenic animals.

Various techniques known in the art can be used to introduce a SOK transgene into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci. USA*, 82:6148 (1985); gene targeting into embryonic stem cells (Thompson et al., *Cell*, 56:313 (1989)); and electroporation of embryos (Lo, *Mol. Cell Biol*, 3:1803 (1983)).

The present invention provides for transgenic animals that carry the SOK transgene in all their nucleated cells, as well as animals that carry the transgene in some, but not all of their nucleated cells, i.e., mosaic animals. The transgene can be integrated as a single transgene or in concatamers, e.g., head-to-head tandems or head-to-tail tandems. For example, transgenic animals can be made in which SOK-1 is under the control of an inducible promoter. The transgene can also be selectively introduced into and/or activated in a particular cell type. Lasko et al., *Proc. Natl. Acad. Sci. USA*, 89:6232 (1992). The regulatory sequences required for such a cell-type specific activation will depend upon the particular cell type of interest, and will be apparent to those of skill in the art.

Vectors containing some nucleotide sequences homologous to an endogenous SOK gene can be designed for the purpose of integrating via homologous recombination into the endogenous gene and disrupting its function, i.e., making "knockout mice." The transgene also can be selectively introduced into a particular cell type, thus inactivating the endogenous SOK-1 gene in only that cell type. See Gu et al., *Science*, 265:103 (1984). The regulatory sequences required for such a cell-type specific inactivation will depend upon the particular cell type of interest, and will be apparent to those of skill in the art.

Once transgenic animals have been generated, the expression of the recombinant SOK gene can be assayed utilizing standard techniques. Initial screening can be accomplished by Southern blot analysis or PCR techniques to analyze animal tissues to assay whether integration of the transgene has taken place. The level of mRNA expression of the transgene in the tissues of the transgenic animals can also be assessed using techniques which include, but are not limited to, Northern blot analysis of tissue samples obtained from the animal, in situ hybridization analysis, and RT-PCR. Samples of tissues expressing SOK can also be evaluated immunocytochemically using antibodies specific for the SOK transgene product.

Therapeutic Compositions

The therapeutic compositions of the invention can be used to increase SOK expression or activity in a patient to treat a pathological condition, e.g., a condition associated with a proliferative response, such as inflammatory responses, cancer, atherosclerosis or ballon angioplasty-induced injury to blood vessels. The therapeutic compositions of the invention can also be used to treat pathological conditions associated with NKFB expression, such as transplant rejection, post ischemic injury, and the response to viral infection. These compositions can contain the polypeptides or DNAs of the invention, including SOK-1 or a fragment thereof, or a kinase inactive mutant of SOK-1. Polypeptides can be purified by methods that are known to those skilled in the art. Ausubel et al., *Current Protocols in Molecular Biology*, John Wiley & Sons, New York, 1995. DNAs can be administered in a manner allowing their uptake and expression by cells in vivo. DNAs can be administered to the patient by standard vectors and/or gene delivery systems. Suitable gene delivery systems include liposomes, biolistic transfer, receptor-mediated delivery systems, naked DNA and viral vectors such as herpes viruses, retroviruses, adenoviruses and adeno-associated viruses. The polypeptides and DNAs of the invention are administered with a pharmaceutically acceptable carrier, and are formulated according to procedures that are well known to those skilled in the art.

Parenteral administration, such as intravenous, subcutaneous, intramuscular or intraperitoneal delivery routes can be used to deliver the therapeutic compositions of the invention. Dosages for particular patients depend upon many factors, including the patient's size, body surface area, age, the particular substance to be administered, time and route of administration, general health and other drugs being administered concurrently. The amount of therapeutic composition to be administered to a patient can be in the range of 1 to 1000 µg/kg of body weight, e.g., 10 to 500, or 20 to 200 µg/kg of body weight. A typical dose of polypeptide or DNA to be administered to a patient is 100 µg per kilogram of body weight.

Diagnostic Applications

Anti-SOK-1 antibodies can be used to assay tissues for SOK-1; elevated SOK-1 levels may be indicative of cell stress caused, e.g., by ischemia resulting from insults such as stroke and myocardial infarction. Immunoassays using anti-SOK-1 antibody are carried out by standard techniques; e.g., the antibody can be labelled with a detectable label and contacted with a tissue sample under conditions which allow immune complexes to form. The uncomplexed labelled antibody is removed, and labelled immune complexes measured as a measure of SOK-1 in the sample. Immunoassays that can be performed using SOK-1 antibodies are well known to those skilled in the art. See e.g., Ausubel et al., *Current Protocol in Molecular Biology* 2:11:2, John Wiley & Sons, 1995. Immunoassays can utilize radioactive, enzyme-based, or chemiluminescent labels.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 1975 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: Coding Sequence
        ( B ) LOCATION: 127...1404

( x i ) SEQUENCE DESCRIPTION: SEQ ID NO:1:

```
CACCGAGCGC  CCCTGGTGTC  CCTCGTAGTG  GACTGACGCC  GCAGGGCGAG  CTAGCCGGCT      60

CCGCGCCTCT  CCGCGGATCC  AGACGCCTCC  TGGGGCTGCT  GGCGGAGGGT  CTGAGGCGGC     120

GCGGCC ATG GCT CAC CTC CGG GGA TTT GCA AAC CAG CAC TCT CGA GTG            168
       Met Ala His Leu Arg Gly Phe Ala Asn Gln His Ser Arg Val
        1               5                  10

GAC CCT GAG GAG CTC TTC ACC AAG CTC GAC CGC ATT GGC AAG GGC TCG           216
Asp Pro Glu Glu Leu Phe Thr Lys Leu Asp Arg Ile Gly Lys Gly Ser
 15              20                  25                  30

TTT GGG GAG GTC TAC AAG GGC ATC GAT AAC CAC ACA AAG GAG GTG GTG           264
Phe Gly Glu Val Tyr Lys Gly Ile Asp Asn His Thr Lys Glu Val Val
                 35                  40                  45

GCC ATC AAG ATC ATC GAC CTG GAG GAG GCC GAG GAT GAG ATC GAG GAC           312
Ala Ile Lys Ile Ile Asp Leu Glu Glu Ala Glu Asp Glu Ile Glu Asp
             50                  55                  60

ATC CAG CAG GAG ATC ACT GTC CTC AGT CAG TGC GAC AGC CCC TAC ATC           360
Ile Gln Gln Glu Ile Thr Val Leu Ser Gln Cys Asp Ser Pro Tyr Ile
         65                  70                  75
```

| | | | | | | | | | | | | | | | | |
|---|---|---|---|---|---|---|---|---|---|---|---|---|---|---|---|---|
| ACC | CGC | TAC | TTT | GGC | TCC | TAC | CTA | AAG | AGC | ACC | AAG | CTA | TGG | ATC | ATC | 408 |
| Thr | Arg | Tyr | Phe | Gly | Ser | Tyr | Leu | Lys | Ser | Thr | Lys | Leu | Trp | Ile | Ile | |
| | 80 | | | | 85 | | | | | 90 | | | | | | |
| ATG | GAG | TAC | CTG | GGC | GGC | GGC | TCA | GCA | CTG | GAC | TTG | CTT | AAA | CCA | GGT | 456 |
| Met | Glu | Tyr | Leu | Gly | Gly | Gly | Ser | Ala | Leu | Asp | Leu | Leu | Lys | Pro | Gly | |
| 95 | | | | | 100 | | | | | 105 | | | | | 110 | |
| CCC | CTG | GAG | GAG | ACA | TAC | ATT | GCC | ACG | ATC | CTG | CGG | GAG | ATT | CTG | AAG | 504 |
| Pro | Leu | Glu | Glu | Thr | Tyr | Ile | Ala | Thr | Ile | Leu | Arg | Glu | Ile | Leu | Lys | |
| | | | | 115 | | | | | 120 | | | | | 125 | | |
| GGC | CTG | GAT | TAT | CTG | CAC | TCC | GAA | CGC | AAG | ATC | CAC | CGA | GAC | ATC | AAA | 552 |
| Gly | Leu | Asp | Tyr | Leu | His | Ser | Glu | Arg | Lys | Ile | His | Arg | Asp | Ile | Lys | |
| | | | | 130 | | | | | 135 | | | | | 140 | | |
| GCT | GCC | AAC | GTG | CTA | CTC | TCG | GAG | CAG | GGT | GAC | GTG | AAG | CTG | GCG | GAC | 600 |
| Ala | Ala | Asn | Val | Leu | Leu | Ser | Glu | Gln | Gly | Asp | Val | Lys | Leu | Ala | Asp | |
| | | 145 | | | | | 150 | | | | | 155 | | | | |
| TTT | GGG | GTA | GCA | GGG | CAG | CTC | ACA | GAC | ACG | CAG | ATT | AAG | AGG | AAC | ACA | 648 |
| Phe | Gly | Val | Ala | Gly | Gln | Leu | Thr | Asp | Thr | Gln | Ile | Lys | Arg | Asn | Thr | |
| | | 160 | | | | | 165 | | | | | 170 | | | | |
| TTC | GTG | GGC | ACC | CCC | TTC | TGG | ATG | GCA | CCT | GAG | GTC | ATC | AAG | CAG | TCG | 696 |
| Phe | Val | Gly | Thr | Pro | Phe | Trp | Met | Ala | Pro | Glu | Val | Ile | Lys | Gln | Ser | |
| 175 | | | | | 180 | | | | | 185 | | | | | 190 | |
| GCC | TAC | GAC | TTC | AAG | GCT | GAC | ATC | TGG | TCC | CTG | GGC | ATC | ACA | GCC | ATC | 744 |
| Ala | Tyr | Asp | Phe | Lys | Ala | Asp | Ile | Trp | Ser | Leu | Gly | Ile | Thr | Ala | Ile | |
| | | | | 195 | | | | | 200 | | | | | 205 | | |
| GAG | CTG | GCC | AAG | GGG | GAG | CCT | CCA | AAC | TCT | GAC | CTC | CAC | CCC | ATG | CGC | 792 |
| Glu | Leu | Ala | Lys | Gly | Glu | Pro | Pro | Asn | Ser | Asp | Leu | His | Pro | Met | Arg | |
| | | | 210 | | | | | 215 | | | | | 220 | | | |
| GTC | CTG | TTC | CTG | ATT | CCC | AAG | AAC | AGC | CCA | CCC | ACA | CTG | GAG | GGC | CAG | 840 |
| Val | Leu | Phe | Leu | Ile | Pro | Lys | Asn | Ser | Pro | Pro | Thr | Leu | Glu | Gly | Gln | |
| | | | 225 | | | | | 230 | | | | | 235 | | | |
| CAC | AGC | AAG | CCC | TTC | AAG | GAG | TTC | GTG | GAG | GCC | TGC | CTC | AAC | AAA | GAC | 888 |
| His | Ser | Lys | Pro | Phe | Lys | Glu | Phe | Val | Glu | Ala | Cys | Leu | Asn | Lys | Asp | |
| | 240 | | | | | 245 | | | | | 250 | | | | | |
| CCC | CGA | TTC | CGG | CCC | ACG | GCC | AAG | GAG | CTC | CTG | AAG | CAC | AAG | TTC | ATC | 936 |
| Pro | Arg | Phe | Arg | Pro | Thr | Ala | Lys | Glu | Leu | Leu | Lys | His | Lys | Phe | Ile | |
| 255 | | | | | 260 | | | | | 265 | | | | | 270 | |
| ACA | CGC | TAC | ACC | AAG | AAG | ACC | TCC | TTC | CTC | ACG | GAG | CTC | ATC | GAC | CGC | 984 |
| Thr | Arg | Tyr | Thr | Lys | Lys | Thr | Ser | Phe | Leu | Thr | Glu | Leu | Ile | Asp | Arg | |
| | | | | 275 | | | | | 280 | | | | | 285 | | |
| TAT | AAG | CGC | TGG | AAG | TCA | GAG | GGG | CAT | GGC | GAG | GAG | TCC | AGC | TCT | GAG | 1032 |
| Tyr | Lys | Arg | Trp | Lys | Ser | Glu | Gly | His | Gly | Glu | Glu | Ser | Ser | Ser | Glu | |
| | | | 290 | | | | | 295 | | | | | 300 | | | |
| GAC | TCT | GAC | ATT | GAT | GGC | GAG | GCG | GAG | GAC | GGG | GAG | CAG | GGC | CCC | ATC | 1080 |
| Asp | Ser | Asp | Ile | Asp | Gly | Glu | Ala | Glu | Asp | Gly | Glu | Gln | Gly | Pro | Ile | |
| | | 305 | | | | | 310 | | | | | 315 | | | | |
| TGG | ACG | TTC | CCC | CCT | ACC | ATC | CGG | CCG | AGT | CCA | CAC | AGC | AAG | CTT | CAC | 1128 |
| Trp | Thr | Phe | Pro | Pro | Thr | Ile | Arg | Pro | Ser | Pro | His | Ser | Lys | Leu | His | |
| | 320 | | | | | 325 | | | | | 330 | | | | | |
| AAG | GGG | ACG | GCC | CTG | CAC | AGT | TCA | CAG | AAG | CCT | GCG | GAC | GCC | GTC | AAG | 1176 |
| Lys | Gly | Thr | Ala | Leu | His | Ser | Ser | Gln | Lys | Pro | Ala | Asp | Ala | Val | Lys | |
| 335 | | | | | 340 | | | | | 345 | | | | | 350 | |
| AGG | CAG | CCG | AGG | TCC | CAG | TGC | CTG | TCC | ACG | CTG | GTC | CGG | CCC | GTC | TTC | 1224 |
| Arg | Gln | Pro | Arg | Ser | Gln | Cys | Leu | Ser | Thr | Leu | Val | Arg | Pro | Val | Phe | |
| | | | | 355 | | | | | 360 | | | | | 365 | | |
| GGA | GAG | CTC | AAA | GAG | AAG | CAC | AAG | CAG | AGC | GGC | GGG | AGC | GTG | GGT | GCG | 1272 |
| Gly | Glu | Leu | Lys | Glu | Lys | His | Lys | Gln | Ser | Gly | Gly | Ser | Val | Gly | Ala | |
| | | | | 370 | | | | | 375 | | | | | 380 | | |
| CTG | GAG | GAG | CTG | GAG | AAC | GCC | TTC | AGC | CTG | GCC | GAG | GAG | TCC | TGC | CCC | 1320 |
| Leu | Glu | Glu | Leu | Glu | Asn | Ala | Phe | Ser | Leu | Ala | Glu | Glu | Ser | Cys | Pro |  |
| | | | | 385 | | | | | 390 | | | | | 395 | | |

| | | | | | | | | | | | | | | |
|---|---|---|---|---|---|---|---|---|---|---|---|---|---|---|
| GGC | ATC | TCA | GAC | AAG | CTG | ATG | GTG | CAC | CTG | GTG | GAG | CGA | GTG | CAG | AGG | 1368
| Gly | Ile | Ser | Asp | Lys | Leu | Met | Val | His | Leu | Val | Glu | Arg | Val | Gln | Arg |
| | 400 | | | | | 405 | | | | | 410 | | | | |
| TTT | TCA | CAC | AAC | AGA | AAC | CAC | CTG | ACA | TCC | ACC | CGC | TGAAGCGCAC | TGCTGT | 1420
| Phe | Ser | His | Asn | Arg | Asn | His | Leu | Thr | Ser | Thr | Arg | | |
| 415 | | | | | 420 | | | | | 425 | | | |

```
TCAGATAGGG GACGGAAGGT CGTTTGTTTT TGTTCTGAGC TCCATAAGAA CTGTGCTGAC   1480
TTGGAAGGTG CCCTGTGCTA TGTCGTGCCT GCAGGGACAC GTCGGATCCC GTGGGCCTCA   1540
CATGCCAGGT CACCAGGTCA CCGTCTCCTT CCACCCCTGC AGTGTGCTGT TGTGCACGTC   1600
AGGACGCTGT TCTCTATGCC ACTGCCTCCT CCCTCTCCTG GCCCAGCAGT ATTGCTCACG   1660
GGGGCTCCAG CCGCCGGCGT GGCCCTCATG AGCTACGCCT GGGTCTTCTG CAGACTCATG   1720
CAGCCCTATG GCCGCTCAGA CCAAGGCGCA GAGCAACTAT CAGGGCATGC TCTGCCTCCT   1780
CCTCCCATTG AGGTGGGGAG AGGCAACAGG GCAGCCCCCA GAGGAGTGTC CTGGCCGCTG   1840
TCTCCCGGGC CCATGATGGC CATAGATTTG CCTTGTGGTG TTCCATCAGG TACTGTGTCT   1900
GCTCATAAGT ACTTGTGTCA TCCAGAATGT TTTGTTTTTT AAGAAAATTG AATTACTTGT   1960
TTCCTGAAAA AAAAA                                                    1975
```

( 2 ) INFORMATION FOR SEQ ID NO:2:

( i ) SEQUENCE CHARACTERISTICS:
        ( A ) LENGTH: 426 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:2:

```
Met Ala His Leu Arg Gly Phe Ala Asn Gln His Ser Arg Val Asp Pro
 1               5                  10                  15
Glu Glu Leu Phe Thr Lys Leu Asp Arg Ile Gly Lys Gly Ser Phe Gly
                20                  25                  30
Glu Val Tyr Lys Gly Ile Asp Asn His Thr Lys Glu Val Val Ala Ile
            35                  40                  45
Lys Ile Ile Asp Leu Glu Glu Ala Glu Asp Glu Ile Glu Asp Ile Gln
    50                  55                  60
Gln Glu Ile Thr Val Leu Ser Gln Cys Asp Ser Pro Tyr Ile Thr Arg
65                  70                  75                  80
Tyr Phe Gly Ser Tyr Leu Lys Ser Thr Lys Leu Trp Ile Ile Met Glu
                85                  90                  95
Tyr Leu Gly Gly Gly Ser Ala Leu Asp Leu Leu Lys Pro Gly Pro Leu
                100                 105                 110
Glu Glu Thr Tyr Ile Ala Thr Ile Leu Arg Glu Ile Leu Lys Gly Leu
            115                 120                 125
Asp Tyr Leu His Ser Glu Arg Lys Ile His Arg Asp Ile Lys Ala Ala
    130                 135                 140
Asn Val Leu Leu Ser Glu Gln Gly Asp Val Lys Leu Ala Asp Phe Gly
145                 150                 155                 160
Val Ala Gly Gln Leu Thr Asp Thr Gln Ile Lys Arg Asn Thr Phe Val
                165                 170                 175
Gly Thr Pro Phe Trp Met Ala Pro Glu Val Ile Lys Gln Ser Ala Tyr
                180                 185                 190
Asp Phe Lys Ala Asp Ile Trp Ser Leu Gly Ile Thr Ala Ile Glu Leu
            195                 200                 205
```

```
Ala Lys Gly Glu Pro Pro Asn Ser Asp Leu His Pro Met Arg Val Leu
    210             215             220
Phe Leu Ile Pro Lys Asn Ser Pro Pro Thr Leu Glu Gly Gln His Ser
225             230             235                         240
Lys Pro Phe Lys Glu Phe Val Glu Ala Cys Leu Asn Lys Asp Pro Arg
                245             250             255
Phe Arg Pro Thr Ala Lys Glu Leu Leu Lys His Lys Phe Ile Thr Arg
            260             265             270
Tyr Thr Lys Lys Thr Ser Phe Leu Thr Glu Leu Ile Asp Arg Tyr Lys
        275             280             285
Arg Trp Lys Ser Glu Gly His Gly Glu Glu Ser Ser Ser Glu Asp Ser
    290             295             300
Asp Ile Asp Gly Glu Ala Glu Asp Gly Glu Gln Gly Pro Ile Trp Thr
305             310             315                         320
Phe Pro Pro Thr Ile Arg Pro Ser His Ser Lys Leu His Lys Gly
                325             330             335
Thr Ala Leu His Ser Ser Gln Lys Pro Ala Asp Ala Val Lys Arg Gln
            340             345             350
Pro Arg Ser Gln Cys Leu Ser Thr Leu Val Arg Pro Val Phe Gly Glu
        355             360             365
Leu Lys Glu Lys His Lys Gln Ser Gly Gly Ser Val Gly Ala Leu Glu
    370             375             380
Glu Leu Glu Asn Ala Phe Ser Leu Ala Glu Glu Ser Cys Pro Gly Ile
385             390             395                         400
Ser Asp Lys Leu Met Val His Leu Val Glu Arg Val Gln Arg Phe Ser
                405             410             415
His Asn Arg Asn His Leu Thr Ser Thr Arg
            420             425
```

( 2 ) INFORMATION FOR SEQ ID NO:3:

( i ) SEQUENCE CHARACTERISTICS:
        ( A ) LENGTH: 268 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Pro Lys Lys Lys Tyr Thr Arg Phe Glu Lys Ile Gly Gln Gly Ala Ser
1               5               10                          15
Gly Thr Val Tyr Thr Ala Met Asp Val Ala Thr Gly Gln Glu Val Ala
            20              25              30
Ile Lys Gln Met Asn Leu Gln Gln Gln Pro Lys Lys Glu Leu Ile Ile
        35              40              45
Asn Glu Ile Leu Val Met Arg Glu Asn Lys Asn Pro Asn Ile Val Asn
    50              55              60
Tyr Leu Asp Ser Tyr Leu Val Gly Asp Glu Leu Trp Val Val Met Glu
65              70              75                          80
Tyr Leu Ala Gly Gly Ser Leu Thr Asp Val Val Thr Glu Thr Cys Met
                85              90              95
Asp Glu Gly Gln Ile Ala Ala Val Cys Arg Glu Cys Leu Gln Ala Leu
            100             105             110
Glu Phe Leu His Ser Asn Gln Val Ile His Arg Asp Ile Lys Ser Asp
        115             120             125
```

```
Asn  Ile  Leu  Leu  Gly  Met  Asp  Gly  Ser  Val  Lys  Leu  Thr  Asp  Phe  Gly
     130                 135                      140

Phe  Cys  Ala  Gln  Ile  Thr  Pro  Glu  Gln  Ser  Lys  Arg  Ser  Thr  Met  Val
145                      150                 155                           160

Gly  Thr  Pro  Tyr  Trp  Met  Ala  Pro  Glu  Val  Thr  Arg  Lys  Ala  Tyr
                    165                      170                 175

Gly  Pro  Lys  Val  Asp  Ile  Trp  Ser  Leu  Gly  Ile  Met  Ala  Ile  Glu  Met
               180                      185                      190

Ile  Glu  Gly  Glu  Pro  Pro  Tyr  Leu  Asn  Glu  Asn  Pro  Leu  Arg  Ala  Leu
          195                      200                 205

Tyr  Leu  Ile  Ala  Thr  Asn  Gly  Thr  Pro  Glu  Leu  Gln  Asn  Pro  Glu  Lys
     210                      215                      220

Leu  Ser  Ala  Ile  Phe  Arg  Asp  Phe  Leu  Asn  Arg  Cys  Leu  Glu  Met  Asp
225                      230                 235                           240

Val  Glu  Lys  Arg  Gly  Ser  Ala  Lys  Glu  Leu  Leu  Gln  His  Gln  Phe  Leu
               245                      250                      255

Lys  Ile  Ala  Lys  Pro  Leu  Ser  Ser  Leu  Thr  Pro  Leu
               260                 265
```

( 2 ) INFORMATION FOR SEQ ID NO:4:

( i ) SEQUENCE CHARACTERISTICS:
        ( A ) LENGTH: 271 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Pro  Ser  Thr  Lys  Tyr  Ala  Asn  Leu  Val  Lys  Ile  Gly  Gln  Gly  Ala  Ser
1                   5                        10                      15

Gly  Gly  Val  Tyr  Thr  Ala  Tyr  Glu  Ile  Gly  Thr  Asn  Val  Ser  Val  Ala
               20                  25                      30

Ile  Lys  Gln  Met  Asn  Leu  Glu  Lys  Gln  Pro  Lys  Lys  Glu  Leu  Ile  Ile
          35                  40                      45

Asn  Glu  Ile  Leu  Val  Met  Lys  Gly  Ser  Lys  His  Pro  Asn  Ile  Val  Asn
     50                       55                      60

Phe  Ile  Asp  Ser  Tyr  Val  Leu  Lys  Gly  Asp  Leu  Trp  Val  Ile  Met  Glu
65                       70                  75                           80

Tyr  Met  Glu  Gly  Gly  Ser  Leu  Thr  Asp  Val  Val  Thr  His  Cys  Ile  Leu
                    85                  90                      95

Thr  Glu  Gly  Gln  Ile  Gly  Ala  Val  Cys  Arg  Glu  Thr  Leu  Ser  Gly  Leu
               100                 105                      110

Glu  Phe  Leu  His  Ser  Lys  Gly  Val  Leu  His  Arg  Asp  Ile  Lys  Ser  Asp
          115                      120                      125

Asn  Ile  Leu  Leu  Ser  Met  Glu  Gly  Asp  Ile  Lys  Leu  Thr  Asp  Phe  Gly
     130                 135                      140

Phe  Cys  Ala  Gln  Ile  Asn  Glu  Leu  Asn  Ile  Lys  Arg  Thr  Thr  Met  Val
145                      150                 155                           160

Gly  Thr  Pro  Tyr  Trp  Met  Ala  Pro  Glu  Val  Val  Ser  Arg  Lys  Glu  Tyr
                    165                      170                 175

Gly  Pro  Lys  Val  Asp  Ile  Trp  Ser  Leu  Gly  Ile  Met  Ile  Ile  Glu  Met
               180                      185                      190

Ile  Glu  Gly  Glu  Pro  Pro  Tyr  Leu  Asn  Glu  Thr  Pro  Leu  Arg  Ala  Leu
          195                      200                 205

Tyr  Leu  Ile  Ala  Thr  Asn  Gly  Thr  Pro  Lys  Leu  Lys  Glu  Pro  Glu  Asn
     210                      215                      220
```

```
Leu  Ser  Ser  Ser  Leu  Lys  Lys  Phe  Leu  Asp  Trp  Cys  Leu  Cys  Val  Glu
225                      230                      235                      240

Pro  Glu  Asp  Arg  Ala  Ser  Ala  Thr  Glu  Leu  Leu  His  Asp  Glu  Tyr  Ile
                    245                      250                      255

Thr  Glu  Ile  Ala  Glu  Ala  Asn  Ser  Ser  Leu  Ala  Pro  Leu  Val  Lys
               260                      265                      270
```

( 2 ) INFORMATION FOR SEQ ID NO:5:

( i ) SEQUENCE CHARACTERISTICS:
        ( A ) LENGTH: 270 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Pro  Glu  Glu  Val  Phe  Asp  Val  Leu  Glu  Lys  Leu  Gly  Glu  Gly  Ser  Tyr
1                   5                    10                       15

Gly  Ser  Val  Tyr  Lys  Ala  Ile  His  Lys  Glu  Thr  Gly  Gln  Ile  Val  Ala
               20                   25                        30

Ile  Lys  Gln  Val  Asx  Val  Glu  Ser  Asp  Leu  Gln  Glu  Ile  Ile  Lys  Glu
          35                   40                        45

Ile  Ser  Ile  Met  Gln  Gln  Cys  Asp  Ser  Pro  His  Val  Val  Lys  Tyr  Tyr
     50                   55                        60

Gly  Ser  Tyr  Phe  Lys  Asn  Thr  Asp  Leu  Trp  Ile  Val  Met  Glu  Tyr  Cys
65                       70                        75                       80

Gly  Ala  Gly  Ser  Val  Ser  Asp  Ile  Ile  Arg  Leu  Arg  Asn  Lys  Thr  Leu
               85                        90                       95

Thr  Glu  Asp  Glu  Ile  Ala  Thr  Ile  Leu  Gln  Ser  Thr  Leu  Lys  Gly  Leu
               100                 105                      110

Glu  Tyr  Leu  His  Phe  Met  Arg  Lys  Ile  His  Arg  Asp  Ile  Lys  Ala  Gly
               115                 120                      125

Asn  Ile  Leu  Leu  Asn  Thr  Glu  Gly  His  Ala  Lys  Leu  Ala  Asp  Phe  Gly
     130                 135                      140

Val  Ala  Gly  Gln  Leu  Thr  Asp  Thr  Met  Ala  Lys  Arg  Asn  Thr  Val  Ile
145                      150                      155                      160

Gly  Thr  Pro  Phe  Trp  Met  Ala  Pro  Glu  Val  Ile  Gln  Glu  Ile  Gly  Tyr
               165                      170                      175

Asn  Cys  Val  Ala  Asp  Ile  Trp  Ser  Leu  Gly  Ile  Thr  Ala  Ile  Glu  Met
               180                      185                      190

Ala  Glu  Gly  Lys  Arg  Pro  Tyr  Ala  Asp  Ile  His  Pro  Met  Arg  Ala  Ile
               195                      200                      205

Phe  Met  Ile  Pro  Thr  Asn  Pro  Pro  Thr  Phe  Arg  Lys  Pro  Glu  Leu
     210                      215                      220

Trp  Ser  Asp  Asn  Phe  Thr  Asp  Phe  Val  Lys  Gln  Cys  Leu  Val  Lys  Ser
225                      230                      235                      240

Pro  Glu  Gln  Arg  Ala  Thr  Ala  Thr  Gln  Leu  Leu  Gln  His  Pro  Phe  Val
                    245                      250                      255

Arg  Ser  Ala  Lys  Gly  Val  Ser  Ile  Leu  Arg  Asp  Leu  Ile  Asn
               260                      265                      270
```

( 2 ) INFORMATION FOR SEQ ID NO:6:

( i ) SEQUENCE CHARACTERISTICS:
        ( A ) LENGTH: 272 amino acids
        ( B ) TYPE: amino acid
        ( D ) TOPOLOGY: linear (ii) MOLECULE TYPE: protein (xi) SEQUENCE DESCRIPTION: SEQ ID NO:6:

| Pro | Ser | Lys | Leu | Tyr | Ser | Ile | Gln | Ser | Cys | Ile | Gly | Arg | Gly | Asn | Phe |
| 1 | | | | 5 | | | | | 10 | | | | | 15 | |

| Gly | Asp | Val | Tyr | Lys | Ala | Val | Asp | Arg | Val | Thr | Gln | Glu | Ile | Val | Ala |
| | | | 20 | | | | 25 | | | | | 30 | | | |

| Ile | Lys | Val | Val | Asn | Leu | Glu | His | Ser | Asp | Glu | Asp | Ile | Glu | Leu | Leu |
| | | 35 | | | | | 40 | | | | | 45 | | | |

| Ala | Gln | Glu | Ile | Phe | Phe | Leu | Ala | Glu | Leu | Lys | Ser | Pro | Leu | Ile | Thr |
| | 50 | | | | | 55 | | | | | 60 | | | | |

| Asn | Tyr | Ile | Ala | Thr | Met | Leu | Glu | Asp | Val | Ser | Met | Trp | Ile | Val | Met |
| 65 | | | | | 70 | | | | | 75 | | | | | 80 |

| Glu | Tyr | Cys | Gly | Gly | Gly | Ser | Cys | Ser | Asp | Leu | Leu | Lys | Arg | Ser | Tyr |
| | | | | 85 | | | | | 90 | | | | | 95 | |

| Val | Asn | Gly | Leu | Pro | Glu | Glu | Lys | Val | Ser | Phe | Ile | Ile | His | Glu | Val |
| | | | 100 | | | | | 105 | | | | | 110 | | |

| Thr | Leu | Gly | Leu | Lys | Tyr | Leu | His | Glu | Gln | Arg | Lys | Ile | His | Arg | Asp |
| | | | 115 | | | | | 120 | | | | | 125 | | |

| Ile | Lys | Ala | Ala | Asn | Ile | Leu | Ile | Asn | Glu | Glu | Gly | Met | Val | Lys | Leu |
| | | 130 | | | | | 135 | | | | | 140 | | | |

| Gly | Asp | Phe | Gly | Val | Ser | Gly | His | Ile | Arg | Ser | Thr | Leu | Lys | Arg | Asp |
| 145 | | | | | 150 | | | | | 155 | | | | | 160 |

| Thr | Phe | Val | Gly | Thr | Pro | Tyr | Trp | Met | Ala | Pro | Glu | Val | Val | Cys | Cys |
| | | | | 165 | | | | | 170 | | | | | 175 | |

| Glu | Val | Asp | Gly | Tyr | Asn | Glu | Lys | Ala | Asp | Ile | Trp | Ser | Leu | Gly | Ile |
| | | | 180 | | | | | 185 | | | | | 190 | | |

| Thr | Thr | Tyr | Glu | Leu | Leu | Lys | Gly | Leu | Pro | Pro | Leu | Ser | Lys | Tyr | Asp |
| | | 195 | | | | | 200 | | | | | 205 | | | |

| Pro | Met | Lys | Val | Met | Thr | Asn | Leu | Pro | Lys | Arg | Lys | Pro | Pro | Lys | Leu |
| | 210 | | | | | 215 | | | | | 220 | | | | |

| Gln | Gly | Pro | Phe | Ser | Asp | Ala | Ala | Lys | Asp | Phe | Val | Ala | Gly | Cys | Leu |
| 225 | | | | | 230 | | | | | 235 | | | | | 240 |

| Val | Lys | Thr | Pro | Ala | Asp | Arg | Pro | Ser | Ala | Tyr | Asn | Leu | Leu | Ser | Phe |
| | | | | 245 | | | | | 250 | | | | | 255 | |

| Glu | Phe | Val | Lys | Asn | Ile | Thr | Ile | Thr | Asn | Leu | Lys | Ser | Asp | Val | Asp |
| | | | 260 | | | | | 265 | | | | | 270 | | |

(2) INFORMATION FOR SEQ ID NO:7:

(i) SEQUENCE CHARACTERISTICS:
        (A) LENGTH: 276 amino acids
        (B) TYPE: amino acid
        (D) TOPOLOGY: linear (ii) MOLECULE TYPE: protein (xi) SEQUENCE DESCRIPTION: SEQ ID NO:7:

| Pro | Arg | Asp | Arg | Phe | Glu | Leu | Leu | Gln | Arg | Val | Gly | Ala | Gly | Thr | Tyr |
| 1 | | | | 5 | | | | | 10 | | | | | 15 | |

| Gly | Asp | Val | Tyr | Lys | Ala | Arg | Asp | Thr | Val | Thr | Ser | Glu | Leu | Ala | Ala |
| | | | 20 | | | | 25 | | | | | 30 | | | |

| Val | Lys | Ile | Val | Lys | Leu | Asp | Pro | Gly | Asp | Asp | Ile | Ser | Ser | Leu | Gln |
| | | 35 | | | | | 40 | | | | | 45 | | | |

| Gln | Glu | Ile | Thr | Ile | Leu | Arg | Glu | Cys | Arg | His | Pro | Asn | Val | Val | Ala |
| | 50 | | | | | 55 | | | | | 60 | | | | |

-continued

| Tyr | Ile | Gly | Ser | Tyr | Leu | Arg | Asn | Asp | Arg | Ile | Trp | Ile | Cys | Met | Glu |
| 65 | | | | 70 | | | | | 75 | | | | | | 80 |

| Phe | Cys | Gly | Gly | Gly | Ser | Leu | Gln | Glu | Ile | Tyr | His | Ala | Thr | Gly | Pro |
| | | | | 85 | | | | | 90 | | | | | 95 | |

| Leu | Glu | Glu | Arg | Gln | Ile | Ala | Tyr | Val | Cys | Arg | Glu | Arg | Leu | Lys | Gly |
| | | | 100 | | | | | 105 | | | | | 110 | | |

| Leu | His | His | Leu | His | Ser | Gln | Gly | Lys | Ile | His | Arg | Asp | Ile | Lys | Gly |
| | | 115 | | | | | 120 | | | | | 125 | | | |

| Ala | Asn | Leu | Leu | Leu | Thr | Leu | Gln | Gly | Asp | Val | Lys | Leu | Ala | Asp | Phe |
| | 130 | | | | | 135 | | | | | 140 | | | | |

| Gly | Val | Ser | Gly | Glu | Leu | Thr | Ala | Ser | Val | Ala | Lys | Arg | Arg | Ser | Phe |
| 145 | | | | | 150 | | | | | 155 | | | | | 160 |

| Ile | Gly | Thr | Pro | Tyr | Trp | Met | Ala | Pro | Glu | Val | Ala | Ala | Val | Glu | Arg |
| | | | | 165 | | | | | 170 | | | | | 175 | |

| Lys | Gly | Gly | Tyr | Asn | Glu | Leu | Cys | Asp | Val | Trp | Ala | Leu | Gly | Ile | Thr |
| | | | 180 | | | | | 185 | | | | | 190 | | |

| Ala | Ile | Glu | Leu | Gly | Glu | Leu | Gln | Pro | Pro | Leu | Phe | His | Leu | His | Pro |
| | | 195 | | | | | 200 | | | | | 205 | | | |

| Met | Arg | Ala | Leu | Met | Leu | Met | Ser | Lys | Ser | Ser | Phe | Gln | Pro | Pro | Lys |
| | 210 | | | | | 215 | | | | | 220 | | | | |

| Leu | Arg | Asp | Lys | Thr | Arg | Trp | Thr | Gln | Asn | Phe | His | His | Phe | Leu | Lys |
| 225 | | | | | 230 | | | | | 235 | | | | | 240 |

| Leu | Ala | Leu | Thr | Lys | Asn | Pro | Lys | Lys | Arg | Pro | Thr | Ala | Glu | Lys | Leu |
| | | | | 245 | | | | | 250 | | | | | 255 | |

| Leu | Gln | His | Pro | Phe | Thr | Thr | Gln | Gln | Leu | Pro | Arg | Ala | Leu | Leu | Thr |
| | | | 260 | | | | | 265 | | | | | 270 | | |

| Gln | Leu | Leu | Asp | | | | | | | | | | | | |
| | | | 275 | | | | | | | | | | | | |

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Degenerate primer ( i x ) FEATURE:
        ( B ) LOCATION: 3...3
        ( D ) OTHER INFORMATION: where R at position 3 is A or G
        ( B ) LOCATION: 4...4
        ( D ) OTHER INFORMATION: where Y at position 4 is C or T,
            but not U
        ( B ) LOCATION: 6...6
        ( D ) OTHER INFORMATION: where N at position 6 is Inosine
        ( B ) LOCATION: 12...12
        ( D ) OTHER INFORMATION: where N at position 12 is Inosine
        ( B ) LOCATION: 15...15
        ( D ) OTHER INFORMATION: where N at position 15 is Inosine
        ( B ) LOCATION: 18...18
        ( D ) OTHER INFORMATION: where R at position 18 is A or G ( x i ) SEQUENCE DESCRIPTION: SEQ ID NO:8:

GARYTNATGG CNGTNAARCA        20

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear

```
    (  i  i  ) MOLECULE TYPE: Degenerate primer (  i  x  ) FEATURE:
                ( B ) LOCATION: 3...3
                ( D ) OTHER INFORMATION: where N at position 3 is Inosine
                ( B ) LOCATION: 6...6
                ( D ) OTHER INFORMATION: where N at position 6 is Inosine
                ( B ) LOCATION: 9...9
                ( D ) OTHER INFORMATION: where Y at position 9 is C or T,
                        but not U
                ( B ) LOCATION: 12...12
                ( D ) OTHER INFORMATION: where N at position 12 is Inosine
                ( B ) LOCATION: 15...15
                ( D ) OTHER INFORMATION: where R at position 15 is A or G
                ( B ) LOCATION: 18...18
                ( D ) OTHER INFORMATION: where N at position 18 is Inosine
                ( B ) LOCATION: 20...20
                ( D ) OTHER INFORMATION: where K at position 20 is G or T,
                        but not U
                ( B ) LOCATION: 21...21
                ( D ) OTHER INFORMATION: where R at position 21 is A or G (  x  i  ) SEQUENCE DESCRIPTION: SEQ ID NO:9:

T T N G C N C C Y T   T N A T R T C N C K   R T G                                                      2 3

( 2 ) INFORMATION FOR SEQ ID NO:10:

(  i  ) SEQUENCE CHARACTERISTICS:
                ( A ) LENGTH: 10 base pairs
                ( B ) TYPE: nucleic acid
                ( C ) STRANDEDNESS: single
                ( D ) TOPOLOGY: linear (  i  i  ) MOLECULE TYPE: Kozak sequence (  x  i  ) SEQUENCE DESCRIPTION: SEQ ID NO:10:

G C G G C C A T G G                                                                                    1 0
```

What is claimed is:

1. An isolated Ste20 oxidant stress response kinase (SOK) polypeptide which is encoded by a nucleotide sequence which hybridizes at 68° C. in 5×SSC, 5×Denhardt's solution, and 1.0% SDS followed by washing in 0.2×SSC and 0.1% SDS at room temperature to the nucleotide sequence depicted in SEQ ID NO:1, said polypeptide having the ability to induce cell cycle arrest; and said polypeptide being activated by oxidant stress.

2. The polypeptide of claim 1, wherein said polypeptide is human.

3. The polypeptide of claim 1, wherein said polypeptide is able to bind to an antibody specific for an epitope within the region defined by amino acids 333–426 of SEQ ID NO:2.

4. The polypeptide of claim 1, said polypeptide having the amino acid sequence depicted in SEQ ID NO:2.

5. The polypeptide of claim 1, said polypeptide being Ste20 oxidant stress response kinase-1 (SOK-1) polypeptide.

6. An isolated Ste20 oxidant stress response kinase-1 (SOK-1) polypeptide having an apparent molecular weight of 50 kD on western blot; said protein having an amino-terminal protein kinase domain and a noncatalytic carboxy-terminal domain; said polypeptide having functional activities comprising protein kinase activity; said polypeptide being activated by oxidant stress, depletion of intracellular ATP stores, or phosphorylation; and said polypeptide not being activated by epidermal growth factor (EGF), platelet-derived growth factor (PDGF), tumor necrosis factor-α (TNFα), anisomycin, heat shock, or osmolar stress.

7. A biologically active fragment of Ste20 oxidant stress response kinase-1 (SOK-1) polypeptide, said fragment comprising amino acids 286 to 426 of SEQ ID NO:2, said fragment having the ability to induce cell cycle arrest in a human cell.

8. A biologically active fragment of Ste20 oxidant stress response kinase-1 (SOK-1) polypeptide, said fragment comprising amino acids 286 to 336 of SEQ ID NO:2, said fragment having the ability to induce cell cycle arrest in a human cell.

9. A biologically active fragment of the Ste20 oxidant stress response kinase-1 (SOK-1) polypeptide, said fragment comprising the amino-terminal kinase region amino acids 1 to 285 of SEQ ID NO:2.

10. A therapeutic composition comprising the SOK-1 polypeptide of claim 1, and a pharmaceutically acceptable carrier.

11. A therapeutic composition comprising the SOK-1 polypeptide of claim 6, and a pharmaceutically acceptable carrier.

12. A therapeutic composition comprising the SOK-1 polypeptide fragment of claim 7, and a pharmaceutically acceptable carrier.

13. A therapeutic composition comprising the SOK-1 polypeptide fragment of claim 8, and a pharmaceutically acceptable carrier.

14. A therapeutic composition comprising the SOK-1 polypeptide fragment of claim 9, and a pharmaceutically acceptable carrier.

15. A kinase inactive mutant of Ste20 oxidant stress response kinase-1 (SOK-1) polypeptide, said SOK-1 polypeptide being encoded by a nucleotide sequence which hybridizes at 68° C. in 5×SSC, 5×Denhardt's solution, and 1.0% SDS followed by washing in 0.2×SSC and 0.1% SDS at room temperature to the nucleotide sequence depicted in SEQ ID NO:1, said SOK-1 polypeptide having the ability to induce cell cycle arrest, and said SOK-1 polypeptide being activated by oxidant stress; said mutant of SOK-1 polypeptide having the invariant lysine within the ATP binding site is substituted or deleted, and said mutant having the ability to induce cell cycle arrest.

16. The kinase inactive mutant of claim 15, wherein the SOK-1 polypeptide has the sequence depicted in SEQ ID NO:2 and the mutation is an arginine substitution.

* * * * *